United States Patent
Constantine et al.

(10) Patent No.: US 8,504,304 B2
(45) Date of Patent: *Aug. 6, 2013

(54) PROTEIN-LIGAND NOE MATCHING FOR HIGH-THROUGHPUT STRUCTURE DETERMINATION

(75) Inventors: Keith Lewis Constantine, Langhorne, PA (US); Brian Lee Claus, Lambertville, NJ (US); Malcolm Evan Davis, Lambertville, NJ (US); William Joseph Metzler, Doylestown, PA (US); Luciano Mueller, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/365,347

(22) Filed: Feb. 3, 2012

(65) Prior Publication Data

US 2012/0143580 A1 Jun. 7, 2012

Related U.S. Application Data

(63) Continuation of application No. 11/272,262, filed on Nov. 10, 2005, now Pat. No. 8,150,634.

(60) Provisional application No. 60/627,582, filed on Nov. 12, 2004.

(51) Int. Cl.
*G06F 19/00* (2011.01)
*G01N 33/50* (2006.01)
*G06G 7/48* (2006.01)

(52) U.S. Cl.
USPC .............................. 702/20; 702/19; 703/11

(58) Field of Classification Search
None
See application file for complete search history.

(56) References Cited

PUBLICATIONS

Bartels, H. et al., "GARANT—A General Algorithm for Resonance Assignment of Multidimensional Nuclear Magnetic Resonance Spectra", J. of Computational Chemistry, vol. 18(1), pp. 139-149 (1997).
Brünger, A.T., X-Plor Version 3.1 Manual, Yale University Press, New Haven, CT 1992.
Constantine, K. et al., "Backbone and Side Chain Dynamics of Uncomplexed Human Adipocyte and Muscle Fatty Acid-Binding Proteins", Biochemistry, vol. 37, pp. 7965-7980 (1998).
Constantine, K. et a., "High-resolution solution structure of siamycin II: Novel amphipathic character of a 21-residue peptide that inhibits HIV fusion"; Journal of Biomolecular NMR, vol. 5, pp. 271-286 (1995).
Ewing, T.J. et al., "DOCK 4.0: Search strategies for automated molecular docking of flexible molecule databases", Journal of Computer-Aided Molecular Design, vol. 15, pp. 411-428 (2001).
Ferentz, A. et al., "NMR spectroscopy: a multifaceted approach to macromolecular structure", Quarterly Reviews of Biophysics, vol. 33, pp. 29-65 (2000).
Fletcher, C. M. et al., "Treatment of NOE constraints involving equivalent or nonstereoassigned protons in calculations of biomacromolecular structures", Journal of Biomolecular NMR, vol. 8, pp. 292-310 (1996).
Grishaev, A. et al., "BACUS: A Bayesian protocol for the identification of protein NOESY spectra via unassigned spin systems", Journal of Biomolecular NMR, vol. 28, pp. 1-10 (2004).
Hodsdon, M. et al., "Ligand Binding Alters the Backbone Mobility of intestinal Fatty Acid-Binding Protein as Monitored by $^{15}N$ NMR Relaxation and $^1H$ Exchange", Biochemistry, vol. 36, pp. 2278-2290 (1997).
Hyvönen, M. et al., "Application of Self-Organizing Maps in Conformational Analysis of Lipids", J. Am. Chem. Soc., vol. 123, pp. 810-16 (2001).
Iwadate, M. et al., "$C^\alpha$ and $C^\beta$ carbon-13 chemical shifts in proteins from an empirical database", Journal of Biomolecular NMR, vol. 13, pp. 199-211 (1999).
Kallen, J. et al., "Structural Basis for LFA-1 Inhibition upon Lovastatin Binding to the CD11a I-Domain", Journal Mol. Biol., vol. 292, pp. 1-9 (1999).
Kay, L.E., "NMR studies of protein structure and dynamics", Journal of Magnetic Resonance, vol. 173, pp. 193-207 (2005).
Lane, A., et al., "Improving NMR sensitivity in room temperature and cooled probes with dipolar ions", Journal of Magnetic Resonance, vol. 173, pp. 339-343 (2005).
Last-Barney, K. et al., "Binding Site Elucidation of Hydantoin-Based Antagonists of LFA-1 Using Multidisciplinary Technologies: Evidence for the Allosteric Inhibition of a Protein-Protein Interaction", J. Am. Chem. Soc., vol. 123, pp. 5643-5650 (2001).
Legge, G. et al., "NMR Solution Structure of the Inserted Domain of Human Leukocyte Function Associated Antigen-1", Journal Mol. Biol., vol. 295, pp. 1251-1264 (2000).
Lugovskoy, A., et al., "A Novel Approach for Characterizing Protein Ligand Complexes: Molecular Basis for Specificity of Small-Molecule Bcl-2 Inhibitors", JACS, vol. 124(7), pp. 1234-1240 (2002).
Matthews, S. et al., "The use of osmolytes to facilitate protein NMR spectroscopy", Journal of Biomolecular NMR, vol. 3, pp. 597-600 (1993).
Neuhaus, D. et al., The Nuclear Overhauser Effect in Structural and Conformational Analysis: VCH Publishers: New York, pp. 109.
Nilges, M. et al., "Determination of three-dimensional structures of proteins by simulated annealing with interproton distance restraints. Application to crambin, potato carboxypeptidase inhibitor and barley serine proteinase inhibitor 2", Protein Engineering, vol. 2(1), pp. 27-38 (1988).

(Continued)

*Primary Examiner* — Eric S Dejong
(74) *Attorney, Agent, or Firm* — Stephen C. D'Amico

(57) ABSTRACT

A method of enhancing the throughput and applicability of NMR-based structure determination of protein-ligand complexes is disclosed. The method circumvents the need for protein sequence-specific resonance assignments and combines NMR data analysis and ligand docking methods into an integrated process. In one embodiment, NMR data is used to filter docking results to identify the most consistent binding modes, thereby providing structural information in a high-throughput fashion without the need for assigning protein resonances. Trial assignments for protein-ligand nuclear Overhauser effect (NOE) interactions are also produced by the method.

40 Claims, 8 Drawing Sheets

PUBLICATIONS

Osapay, K. et al., "A New Analysis of Proton Chemical Shifts in Proteins", J. Am. Chem. Soc., vol. 113, pp. 9436-9444 (1991).

Potin, D. et al., "De novo design, synthesis, and in vitro activity of LFA-1 antagonists based on a bicyclic [5.5] hydantoin scaffold", Bioorganic & Medicinal Chemistry Letters, vol. 15, pp. 1161-1164 (2005).

Rieping, W. et al., "Inferential Structure Determination", Science, vol. 309, pp. 303-306 (2005).

Seavey, B. et al., "A relational database for sequence-specific protein NMR data", Journal of Biomolecular NMR, vol. 1, pp. 217-236 (1991).

Wang, B. et al., "Fast semiempirical calculations for nuclear magnetic resonance chemical shifts: A divide-and-conquer approach", Journal of Chemical Physics, vol. 120(24), pp. 11392-11400 (2004)r45.

Shuker, S. et al., "Discovering High-Affinity Ligands for Proteins: SAR by NMR", Science, vol. 274, pp. 1531-1534 (1996).

Han, J. et al., Data Mining: Concepts and Techniques: Morgan Kaufmann: New York, pp. 335-393 (2001).

Cavanaugh, et al. Protein NMR Spectroscopy: Principles and Practice; Academic Press, NY, pp. 235-236 (1996).

Ward, et al., "Protein complexes suited by NMR spectroscopy", Curr. Opin. Biotech., vol. 7, pp. 403-408 (1996).

Hitchens, et al., "MONTE: An automated Monte Carlo based approach to nuclear magnetic resonance assignment of proteins", J. Biomolec. NMR, vol. 25, pp. 1-9 (2003).

Totrov, et al., "Flexible Protein-Ligand Docking by Global Energy Optimization in Internal Coordinates", Proteins: Structure Function and Genetics, vol. 1, lines 215-200, Suppl. (1997).

Bertini, et al., "Combining in Silico Tools and NMR Data to Validate Protein-Ligand Structural Models: Application to Matrix Metalloproteinases", J. Med. Chem., vol. 48, pp. 7544-7559 (2005).

Breeze, Alexander, L., "Isotope-filtered NMR methods for the study of biomolecular structure and interactions", Prog. Nuclear Magnetic Resonance Spectroscopy, vol. 36, pp. 323-372 (2000).

Campbell, et al., "The Two-Dimensional Transferred Nuclear Overhauser Effect: Theory and Practice", Annu. Rev. Biophys. Biomol. Struct., vol. 22, pp. 99-122 (1993).

Clore, et al., "Theory of the Time Dependent Transferred Nuclear Overhauser Effect: Applications to Structural Analysis of Ligand-Protein Complexes in Solution", J. Magnetic Resonance, vol. 53, pp. 423-442 (1983).

Clore, et al., "Theory and Applications of the Transferred Nuclear Overhauser Effect to the Study of the Conformations of Small Ligands Bound to Proteins", J. Magnetic Resonance, vol. 48, pp. 402-417 (1982).

Clore, et al., "Theoretical and computational advances in biomolecular NMR spectroscopy", Curr. Opin. Structural Biol., vol. 12, pp. 146-153 (2002).

Coles, et al., "NMR-based screening technologies", DDT, vol. 8(17), pp. 803-810 (2003).

Constantine, Keith, L., "Evaluation of Site-Directed Spin Labeling for Characterizing Protein-Ligand Complexes Using Simulated Restraints", Biophysical Journal, vol. 81, pp. 1275-1284 (2001).

DePristo, et al., "Heterogeneity and Inaccuracy in Protein Structures Solved by X-Ray Crystallography", Structure, vol. 12, pp. 831-838 (2004).

Farmer, et al., "Localizing the NADP+ binding site on the MurB enzyme by NMR", Nature Structural Biol., vol. 3 (12), pp. 995-997 (1996).

Gronwald et al., "Automated structure determination of proteins by NMR spectroscopy", Prog. Nuclear Magnetic Resonance Spectroscopy, vol. 44, pp. 33-96 (2004).

Güntert, Peter, "Automated NMR protein structure calculation", Prog. Nuclear Magnetic Resonance Spectroscopy, vol. 43, pp. 105-125 (2003).

Hajduk, et al., "Discovery of Potent Nonpeptide Inhibitors of Stromelysin Using SAR by NMR", J. Am. Chem. Soc., vol. 119, pp. 5818-5827 (1997).

Hillisch, et al, "Utility of homology models in the drug discovery process", DDT, vol. 9 (15), pp. 659-669 (2004).

Homans, Steve, W., "NMR Spectroscopy Tools for Structure-Aided Drug Design", Angew. Chem. Int. Ed., vol. 43, pp. 290-300 (2004).

Lesuisse, et al., "SAR and X-ray. A New Approach Combining Fragment-Based Screening and Rational Drug Design: Application to the Discovery of Nanomolar Inhibitors of Src SH2", J. Med. Chem., vol. 45, pp. 2379-2387 (2002).

Mayer, et al., "Characterization of Ligand Binding by Saturation Transfer Difference NMR Spectroscopy", Angew. Chem. Int. Ed., vol. 38 (12), pp. 1784-1788 (2004).

McCoy, et al., "Alignment of weakly interacting molecules to protein surfaces using simulations of chemical shift perturbations", J. Biomolecular NMR, vol. 18, pp. 189-198 (2000).

Medek, et al., "The Use of Differential Chemical Shifts for Determining the Binding Site Location and Orientation of Protein-Bound Ligands", J. Am. Chem. Soc., vol. 122, pp. 1241-1242 (2000).

Medek, et al., "An approach for high-throughput structure determination of proteins by NMR spectroscopy", J. Biomolecular NMR, vol. 18, pp. 229-238 (2000).

Ni, et al., "Use of the Transferred Nuclear Overhauser Effect to Determine the Conformations of Ligands Bound to Proteins", Accounts of Chem. Res., vol. 27 (9), pp. 257-264 (1994).

Oltersdorf, et al., "An inhibitor of Bcl-2 family proteins induces regression of solid tumours", Nature, vol. 435, pp. 677-681 (2005).

Pellecchia, et al., "NMR-based structural characterization of large protein-ligand interactions", J. Biomolecular NMR, vol. 22, pp. 165-173 (2002).

Pellecchia, et al., "NMR in Drug Discovery", vol. 11, pp. 211-219 (2002).

Petros, et al., "Conformation of two non-immunosuppressive FK506 analogs when bound to FKBP by isotope-filtered NMR", FEBS, vol. 308 (3), pp. 309-314 (1992).

Petros, et al., "Discovery of a Potent Inhibitor of the Antiapoptotic Protein Bcl-$x_L$ from NMR and Parallel Synthesis", J. Med. Chem., vol. 49, pp. 656-663 (2006).

Riek, et al., "TROSY and CRINEPT:NMR with large molecular and supramolecular structures in solution", TIBS, vol. 25, pp. 462-468 (2000).

Roberts, et al., "Applications of NMR in drug discovery", DDT, vol. 5 (6), pp. 230-240 (2000).

Schieborr, et al., "How Much NMR Data is Required to Determine a Protein-Ligand Complex Structure?", Chem Bio Chem., vol. 6, pp. 1891-1898 (2005).

Shuker, et al., "Discovering High-Affinity Ligands for Proteins: SAR by NMR", Science, vol. 274, pp. 1531-1534 (1996).

Stockman, et al., "NMR screening techniques in drug discovery and drug design", Prog. Nuclear Magnetic Resonance Spectroscopy, vol. 41, pp. 187-231 (2002).

Tugarinov, et al., "Four-Dimensional NMR Spectroscopy of a 723-Residue Protein: Chemical Shift Assignments and Secondary Structure of Malate Synthase G", J. Am. Chem. Soc., vol. 124, pp. 10025-10035 (2002).

Vajda, et al., "Characterization of protein ligand interaction of sites using experimental and computational methods", Curr. Opin. Drug Dis. Develop., vol. 9 (3), pp. 354-362 (2006).

Villar, et al., "Using NMR for ligand discovery and optimization", Curr. Opin. Chem. Biol., vol. 8, pp. 387-391 (2004).

Zartler, Edward, R. "Fragment-Based Drug Discovery, A Practical Approach", Editors, Edward R. Zartler, Merck & Co., Inc., and Michael J. Shapiro, School of Pharmaceutical Sciences, University of MD., "Application of Protein-Ligand NOE Matching to the Rapid Evaluation of Fragment Binding Poses", Metzler, et al., 5.1 to 5.10, pp. 99-133 (2008).

Brünger, A.T., "A System for X-ray Crystallography and NMR", The Howard Hughes Med. Inst. and Dept. of Mol. Biophysics and Biochemistry, pp. 27-72, 112-114, 271-328 (1992).

Constantine, K.L. et al., "J-Coupling Restraint Potentials for Nonstereospecifically Assigned Methylene Protons and Ensemble-Average Calculations", J. Mag. Res. Series B, vol. 108, pp. 176-184 (1995).

Constantine, K.L. et al., "Protein-Ligand NOE Matching: A High-Throughput Method for Binding Pose Evaluation That Does Not Require Protein NMR Resonance Assignments", J. Am. Chem. Soc., vol. 128, pp. 7252-7263 (2006).

Dobrodumov, A. et al., "Filtering and Selection of Structural Models: Combining Docking and NMR", Proteins: Structure, Function, and Bioinformatics, vol. 53, pp. 18-32 (2003).

Ewing, T.J.A. et al., "Dock 4.0: Search Strategies for Automated Molecular Docking of Flexible Molecule Databases", J. of Comp-Aided Mol. Design, vol. 15, pp. 411-428 (2001).

Güntert, P. et al., "Efficient Computation of Three-Dimensional Protein Structures in Solution from Nuclear Magnetic Resonance Data Using the Program DIANA and the Supporting Programs CALIBA, HABAS and GLOMSA", J. Mol. Biol., vol. 217, pp. 517-530 (1991).

Hajduk, P. et al., "SOS-NMR: A Saturation Transfer NMR-Based Method for Determining the Structures of Protein-Ligand Complexes", J. Am, Chem. Soc., vol. 126, pp. 2390-2398 (2004).

Hus, J.C. et al., "Assignment Strategy for Proteins with Known Structure", J. Mag. Res., vol. 157, pp. 119-123 (2002).

Kitchen, D.B. et al., "Docking and Scoring in Virtual Screening for Drug Discovery: Methods and Applications", Nat. Rev., vol. 3, pp. 935-949 (2004).

Langmead, C.J. et al., "An Expectation/Maximization Nuclear Vector Replacement Algorithm for Automated NMR Resonance Assignments", J. Biomol. NMR, vol. 29, pp. 111-138 (2004).

Meiler, J. et al., Rapid Protein Fold Determination using Unassigned NMR Data, Proc. Natl. Acad. Sci., vol. 100, pp. 15404-15409 (2003).

Metzler, W.J. et al., "The Three-Dimensional Solution Structure of the SH2 Domain from p55$^{blk}$ Kinase", Biochemistry, vol. 35 pp. 6201-6211 (1996).

Papadimitriou et al., Combinatorial Optimization: Algorithms and Complexity, pp. 247-255, Prentice-Hall, Inc., Englewood Cliffs, NJ (1982).

Sitkoff, D. et al., "Density Functional Calculations of Proton Chemical Shifts in Model Peptides", J. Am. Chem. Soc., vol. 119, pp. 12262-12273 (1997).

Wang, B. et al., "Pose Scoring by NMR", J. Am. Chem. Soc., vol. 126, pp. 11430-11431 (2004).

Xu, et al., "Automated Prediction of $^{15}N$, $^{13}C^{\alpha}$, $^{13}C^{\beta}$ and $^{13}C'$ Chemical Shifts in Proteins Using a Density Functional Database", J. of Biomol. NMR, vol. 21, pp. 321-333 (2001).

Xu, et al., "Automated Assignment of Backbone NMR peaks Using Constrained Bipartite Matching", Comput. in Sci. Eng., vol. 4, pp. 50-62 (2002).

Fig. 3

PROTEIN-LIGAND NOE MATCHING FOR HIGH-THROUGHPUT STRUCTURE DETERMINATION

This application is a continuation of U.S. Ser. No. 11/272,262, filed Nov. 10, 2005, now U.S. Pat. No. 8,150,634 which claims benefit to provisional application U.S. Ser. No. 60/627,582 filed Nov. 12, 2004, under 35 U.S.C. 119(e).

FIELD OF THE INVENTION

The present invention relates generally to nuclear magnetic resonance (NMR) methods. More particularly, the invention relates to a high throughput method of determining the structure of a protein-ligand complex using nuclear Overhauser effect (NOE) data, without the need for providing signal assignments for the protein's NMR-active nuclei.

BACKGROUND

The three-dimensional (3D) structures of protein-ligand complexes can be determined by Nuclear Magnetic Resonance (NMR) spectroscopy. Sometimes the protein's 3D structure is known in advance. This circumstance reduces the problem to a matter of determining the binding mode, also referred to as the "pose," of the ligand. A primary method used for structure determination by NMR relies on intermolecular Nuclear Overhauser Effect (NOE) distance restraints between the protein and the ligand. These restraints can be derived from Nuclear Overhauser Effect Spectroscopy (NOESY) NMR experiments, for example, from 3D $^{13}$C-edited, $^{15}$N/$^{13}$C-filtered HSQC-NOESY experiments, or from 2D $^1$H-$^1$H NOESY experiments. In favorable situations, high-resolution binding modes can be determined by this method.

Various methods have been proposed for the structural study of protein-ligand complexes, some of which do not require that protein resonance assignments be made. For example, Hajduk et al. (Hajduk et al. (2004) *J. Am. Chem. Soc.* 126:2390-2398) describe a method purportedly useful for determining the structures of protein-ligand complexes that does not require protein resonance assignments. However, the method of Hajduk et al. is applicable only to weakly binding, soluble ligands, and does not allow for inclusion of protein resonance assignments if they are available, and therefore does not facilitate an iterative refinement process.

Similarly, Meiler & Baker describe a method purportedly useful for identifying a good fit between a set of proposed protein structures and unassigned chemical shifts, NOEs and residual dipolar couplings (Meiler & Baker, (2003) *Proc. Natl. Acad. Sci. USA* 100:15404-15409). The method of Meiler & Baker, however, focuses on protein structure determination and employs a Monte Carlo approach, which is may not generate the optimal results.

Dobrodumov & Gronenborn describe a method purportedly useful for identifying models of protein-protein complexes that give the best match to chemical shift changes and residual dipolar couplings (Dobrodumov & Gronenborn, (2003) *Proteins* 52:18-32). A drawback of this method is that the method requires protein backbone atom NMR assignments, which are sometimes not available. This method is not applicable to protein-ligand (e.g., small molecule) structures.

Xu et al., (Xu et al., (2002) *Comput. Sci. Eng.* 4:50-62), Hus et al., (Hus et al., (2002) *J. Mag. Res.* 157:119-123), and Langemead, & Donald, (Langmead & Donald, (2004) *J. Biomol. NMR* 29:111-138) apparently describe the application of bipartite matching to the problem of assigning protein backbone resonances by matching experimental and predicted NMR data, however these reports do not address the problem of protein-ligand structure determination.

A 3D $^{13}$C-edited, $^{15}$N/$^{13}$C-filtered HSQC-NOESY experimental data set contains exclusively NOE peaks between ligand protons (F3 dimension) and protein $^1$H$^{13}$C groups (F1/F2 dimensions). A 2D $^1$H-$^1$H NOESY spectrum may contain intra-ligand, protein-ligand and protein-protein NOE peaks; these can be distinguished by suitable isotopic labeling schemes. Accordingly, it is recognized that other types of NOE (e.g., 2D $^1$H-$^1$H NOESY) data can readily be incorporated into the procedures described herein.

In order to derive the NOE distance restraints from 3D $^{13}$C-edited, $^{15}$N/$^{13}$C-filtered HSQC-NOESY data, the ligand $^1$H resonances and the protein $^1$H,$^{13}$C resonances must be assigned. The protein resonances must be re-assigned for each new ligand if a series of ligands are to be structurally characterized. While the data for assigning the bound or exchanging ligand can be collected and analyzed in a matter of days, it can take weeks or more to collect and analyze the protein assignment data. In some cases, it is difficult or even impossible to assign the protein resonances. In order to assign the intermolecular NOEs, protein backbone and side-chain assignment data sets must first be collected, processed and analyzed. If the protein assignment step could be bypassed, the utility of NMR for characterizing ligand binding modes would be greatly increased.

Thus what is needed is a high-throughput method of NMR-based structure determination of protein-ligand complexes that does not require protein resonance assignments. The present invention solves this and other problems.

SUMMARY OF THE INVENTION

A method of determining a preferred binding pose of a ligand in a complex comprising a target protein and a ligand using non-scalar magnetic couplings is disclosed. In one embodiment, the method comprises (a) assigning the NMR resonance shifts of the ligand; (b) acquiring an observed NMR peak pattern comprising target protein resonances and ligand resonances, the peak pattern indicating non-scalar couplings between the nuclei of a sample comprising a target protein and a ligand; (c) designating a trial binding pose for the ligand; (d) predicting an NMR peak pattern for the target protein and the ligand in its assigned trial binding pose, (e) finding the optimal match between the predicted peak pattern with the observed peak pattern; (f) based on the match, assigning the trial binding pose a quantitative score representing the degree of similarity between the observed and theoretical peak patterns; (g) repeating steps (c) through (f) a desired number of times to generate a quantitative score for each of one or more binding poses; and (h) evaluating the relative quantitative scores to identify one or more binding poses that are the most consistent with the observed peak pattern.

In embodiments of the present invention, the ligand can be bound to a target protein in the observed peak pattern or the ligand can be exchanging between target-bound and unbound states in the observed peak pattern.

In the present invention, estimates can be obtained for the values of the target protein resonances in a variety of different ways. In one embodiment, the target protein resonances are obtained by employing a method selected from the group consisting of (a) estimating target protein resonance shifts from available data; (b) predicting target protein resonance shifts in silico; and (c) experimentally determining target protein resonances.

The observed NMR peak pattern can further comprise grouping observed target protein resonances on the basis of chemical shift similarity in order identify specific $^1H^{13}C$ groups in the protein that are involved in NOE interactions with the ligand.

The observed NMR peak pattern can be acquired using any of a range of pulse sequences and experimental conditions; in one embodiment of the invention, the observed NMR peak pattern is derived from one or more three-dimensional $^{13}C$-edited, $^{15}N/^{13}C$-filtered. HSQC-NOESY spectra. Further, the observed NMR peak pattern can be simplified by clustering peaks on the basis of the observed protein shifts and, optionally, other criteria, such as known specific residue types associated with certain peaks.

Continuing, the trial ligand binding pose used in the prediction can be generated by performing an in silico operation to define an orientation and conformation of the ligand at a selected location relative to a three-dimensional structure of all or a portion of the target protein. In the invention, the in silico operation can selected from the group consisting of (a) modeling; and (b) an in silico docking procedure, for example, and can employ experimentally-derived data alone or in combination with one or more of a modeling procedure and an in silico docking procedure.

In the present invention, the step of predicting an NMR peak pattern can comprise the steps of (a) obtaining, for example by estimating, predicting and/or experimentally determining, target protein NMR resonance shifts; (b) obtaining and assigning target ligand NMR resonance shifts; (c) selecting a target protein nucleus and a ligand nucleus to form a protein-ligand pair; (d) predicting the peak intensity of a proposed magnetic interaction between each member of the pair; (e) predicting peak shifts for the proposed magnetic interaction; (f) placing each predicted peak in a pattern, the predicted peak being representative of the predicted peak intensity and predicted peak shift; and; and (g) repeating steps (c) through (f) for each of a selected number of protein-ligand pairs. Although the predicted NMR peak pattern can be completely unreliant on experimental protein resonance assignments for the complex under study, in some cases, experimental protein assignment data is available and can be employed. Experimental ligand $^1H$ NMR resonance shifts are determined. In one embodiment of this step, the $^1H$ shifts of the ligand are determined by analyzing data obtained from two-dimensional (2D) double-$^{15}N/^{13}C$-filtered through-bond and through space correlated NMR experiments.

In the predicted NMR peak pattern, the peak intensity can based on intermolecular distances between the groups of nuclei. Additionally, the step of predicting peak shifts can comprise estimating peak shifts by employing one or more of: a databases of known protein chemical shift assignments, an algorithm for chemical shift prediction, and experimental assignment data.

Continuing, in a further embodiment the step of comparing the predicted peak pattern with the observed peak pattern comprises (a) arranging into an equally partitioned bipartite graph groups of protein nuclei observed to give rise to intermolecular non-scalar magnetic couplings and groups of protein nuclei predicted to give rise to intermolecular non-scalar magnetic couplings, wherein the protein groups observed to produce intermolecular non-scalar magnetic couplings are placed in a first subset of nodes, and the protein groups predicted to produce intermolecular non-scalar magnetic couplings placed in a second subset of nodes; and (b) mapping the first subset of nodes to the second subset of nodes.

Additionally, in another embodiment the step of assigning the trial binding pose a quantitative score representing the degree of similarity between the observed and theoretical peak patterns comprises defining a quantitative score for each possible complete matching between the node subsets based on an evaluation of deviations between observed and predicted peak patterns. The step of assigning the quantitative scores, which are subsequently compared to identify one or more binding poses that are most consistent with the observed peak pattern, can comprise employing a combinatorial optimization algorithm to deterministically find an optimal complete matching in polynomial time.

Moreover, the present invention can be employed in a high-throughput structure determination operation.

Thus, it is an object of the present invention to provide a method of determining a preferred binding pose of a ligand in a complex comprising a target protein and a ligand using non-scalar magnetic couplings is disclosed. In one embodiment, the method comprises (a) assigning the NMR resonance shifts of the ligand; (b) acquiring an observed NMR peak pattern comprising target protein resonances and ligand resonances, the peak pattern indicating non-scalar couplings between the nuclei of a sample comprising a target protein and a ligand; (c) designating a trial binding pose for the ligand; (d) predicting an NMR peak pattern for the target protein and the ligand in its assigned trial binding pose, (e) comparing the predicted peak pattern with the observed peak pattern; (f) based on the comparison, assigning the trial binding pose a quantitative score representing the degree of similarity between the observed and theoretical peak patterns; (g) repeating steps (c) through (f) a desired number of times to generate a quantitative score for each of one or more binding poses; and (h) evaluating the quantitative scores to identify one or more binding poses that are the most consistent with the observed peak pattern. This objective is achieved by the present invention.

An object of the invention having been stated hereinabove, other objects will be evident as the description proceeds, when taken in connection with the accompanying Drawings and Examples as described herein.

BRIEF DESCRIPTION OF THE DRAWINGS

FIG. 3 is a bipartite graph representing a 3D $^{13}C$-edited, $^{15}N/^{13}C$-filtered HSQC-NOESY matching problem.

FIG. 6A depicts a completely synthetic data set (comprising "experimental" and predicted peaks) for LFA1/Compound 1. The uncertainties used (generated using equation 5) were set to 0.1 times the standard deviation derived from the Bio Mag Res Bank (BMRB) for each atom type. This test demonstrates that the algorithm is able to identify the target pose, as evidenced by COST=0, using ideal data.

FIG. 6B depicts a real data set for LFA1/Compound 1. The predicted chemical shifts were set to the mean values present in the BMRB, and the uncertainties used were set to 0.5 times the standard deviation derived from the BMRB for each atom type. The best scoring mode has an RMSD of 0.66 Å to the target.

FIG. 6C depicts a real data set for mFABP/Compound 2. The predicted chemical shifts were set to their experimental values if the protein atom/group was assigned, otherwise the mean values present in the BMRB was used. The uncertainties used were set to 0.5 times the standard deviation. The best scoring mode has an RMSD of 0.70 Å to the target.

FIG. 6D depicts a real data set for mFABP/Compound 2. The predicted chemical shifts were set to the mean values present in the BMRB, and the standard deviations used were set to 0.5 times the standard deviation derived from the BMRB for each atom type. The best scoring mode has an RMSD of 1.11 Å to the target.

DETAILED DESCRIPTION OF THE INVENTION

Figure 1:
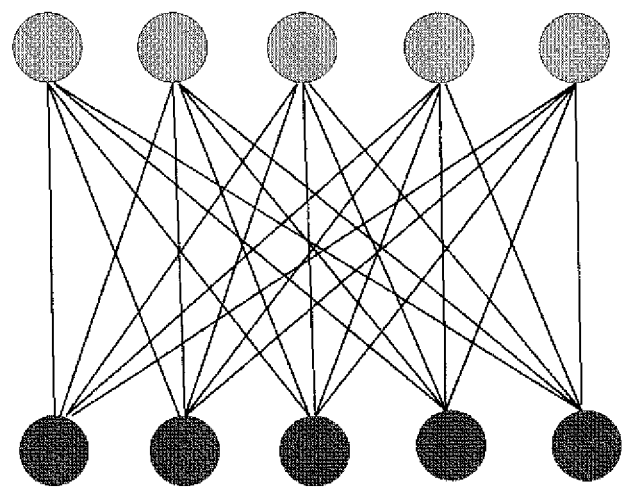
FIG. 1 is diagram depicting a completely connected bipartite graph with N=5.

In one aspect, the present invention facilitates the use of data provided by experiments that reveal intermolecular NOE interactions, such as a 3D $^{13}$C-edited, $^{15}$N/$^{13}$C-filtered HSQC-NOESY experiment, to "score" binding modes sampled by an appropriate docking algorithm without requiring protein resonance assignments. In one embodiment of the invention, for each binding mode sampled, the observed (referred to herein interchangeable with the term "experimental") pattern of NOE peaks is matched to the predicted (referred to herein interchangeably with the term "theoretical") pattern of NOE peaks using a combinatorial optimization algorithm. The quality of this match defines the "NMR score" (also referred to herein as the "NMR cost") of each sampled binding mode, and this cost is used to identify the binding modes that are most consistent with the data. This approach eliminates the requirement for protein assignments and explicit distance restraints. As described herein, the algorithm can also predict protein assignments from which explicit distance restraints can subsequently be derived. These restraints can then be incorporated into a docking procedure, thereby facilitating an iterative refinement process.

It is noted that in embodiments of the present methods, peak predictions and/or observations can be ascribed to either individual atoms or nuclei or groups of atoms or nuclei that are magnetically similar. Magnetically similar atoms or nuclei are atoms nuclei that are present in magnetic similar environments, which thereby give rise to peaks having a similar chemical shift. Thus, magnetically similar atoms or nuclei can be grouped together and treated as an individual unit. It is therefore implicit in the following description that when the term atom is recited, unless explicitly stated or unless context demands otherwise, the term "atom" is used interchangeably with the term group, which refers to a collection of magnetically similar atoms.

I. Definitions and Notation

Following long-standing patent law convention, the terms "a" and "an" mean "one or more" when used in this application, including the claims.

As used herein, the terms "observed peak," "observed peak pattern," "experimental peak," "experimentally observed peak" and "experimentally observed peak pattern" are used interchangeably and mean an NMR peak or peak pattern that was generated by acquiring a degree of experimental data.

As used herein, the terms "theoretical peak," "theoretical peak pattern," "predicted peak," and "predicted observed peak pattern" are used interchangeably and mean an NMR peak or peak pattern that was not generated by acquiring experimental protein assignments.

As used herein, the terms "score" and "cost" are used interchangeably and mean a value that reflects the degree of similarity between a predicted NMR peak pattern and an observed NMR peak pattern, with a higher cost indicating greater dissimilarity.

As used herein, the term "NPAT" refers to the number of protein groups that could give rise to intermolecular non-scalar couplings.

As used herein, the term "NLAT" refers to the number of resolved and assigned ligand $^1$H groups.

As used herein, the term "NTPK" refers to the number of peaks predicted for a given pose.

As used herein, the term "NEAS" refers to the number of protein $^1$H-$^{13}$C groups identified by clustering the peaks in one or more experimental 3D $^{13}$C-edited, $^{15}$N/$^{13}$C-filtered HSQC-NOESY spectra.

As used herein, the term "{PAT$_i$}" refers to a set of protein atoms that could give rise to an NOE; i=1 to NPAT.

As used herein, the term "{LAT$_j$}" refers to a set of resolved, assigned ligand protons/groups; j=1 to NLAT.

As used herein, the term "{EPK$_m$}" refers to a set of all experimental peaks; m=1 to NEPK.

As used herein, the term "H1EPK$_m$" refers to the experimental $^1$H chemical shift of experimental peak m.

As used herein, the term "C13EPK$_m$" refers to the experimental $^{13}$C chemical shift of experimental peak m.

As used herein, the term "IEPK$_m$" refers to the experimental intensity of experimental peak m expressed as an integer.

As used herein, the term "{EAS$_k$}" refers to a set of possible experimental $^1$H,$^{13}$C assignment pairs and unassigned nodes; k=1 to N. These are not initially associated with any specific protein atom/group.

As used herein, the term "H1EAS$_k$" refers to the experimental $^1$H chemical shift of experimental atom/group k.

As used herein, the term "C13EAS$_k$" refers to the experimental $^{13}$C chemical shift of experimental atom/group k.

As used herein, the term "{TPK$_n$}" refers to a set of all theoretical peaks for a given binding mode; n=1 to NTPK.

As used herein, the term "H1TPK$_n$" refers to the theoretical $^1$H chemical shift of theoretical peak n.

As used herein, the term "σH$_n$" refers to the uncertainty of theoretical $^1$H chemical shift of theoretical peak n.

As used herein, the term "C13TPK$_n$" refers to the theoretical $^{13}$C chemical shift of theoretical peak n.

As used herein, the term "σC$_n$" refers to the uncertainty of theoretical $^{13}$C chemical shift of theoretical peak n.

As used herein, the term "ITPK$_n$" refers to the theoretical intensity of theoretical peak n expressed as an integer.

As used herein, the term "$\{TAS_q\}$" refers to a set of possible theoretical $^1H,^{13}C$ assignment pairs and unassigned nodes; q=1 to N.

As used herein, the term "$H1TAS_q$" refers to the theoretical $^1H$ chemical shift of theoretical atom/group q.

As used herein, the term "$C13TAS_q$" refers to the theoretical $^{13}C$ chemical shift of theoretical atom/group q.

II. Possible Assumptions

In the present invention, one or more assumptions can be made. Some are requirements of the method, while others are not absolute requirements. These latter assumptions can simplify an analysis and can be employed to adapt the invention to situations when different amounts and types of data are available. It is noted that these latter assumptions need not be made in every application of the method, and that various combinations of following assumptions can be made in any single application of the invention. Further, the following description of possible assumptions can be supplemented by any other assumption not described explicitly herein, but which can facilitate the application of the invention.

It is assumed that one or more 3D structures and/or structural models of the target protein are available. It can, but need not, be assumed that one or more 3D structures of the protein target can be treated as flexible during the generation of theoretical protein/ligand poses. Conversely, it can be assumed that one or more 3D structures of the protein target can be treated as a rigid member during the generation of theoretical protein/ligand poses It is assumed that there is a set of $^1H^{13}C$ groups in the protein that could give rise to intermolecular NOEs to the ligand. This set may comprise all $^1H^{13}C$ groups in the protein, or it may be restricted to residues known to be in the binding site, type-specifically labeled residues, or other distinguishable group of residues. This set of protein atoms or groups of protein atoms can be denoted $\{PAT_i\}$; i=1, ..., NPAT. These groups may, but need not, be described by NMR peaks that have been specifically assigned. This assumption can be useful in the early stages of an application of the present invention to provide a point from which to start an analysis.

It is assumed that there is a set of ligand $^1H$ atoms or groups. These atoms or groups are described by resolved and assigned NMR peaks. This set can be denoted $\{LAT_j\}$; j= 1, ..., NLAT.

III. Hardware and Software Useful in the Present Invention

The present invention is adaptable to many hardware and software configurations. For example, the present invention can be implemented using a high field NMR spectrometer, equipped with a $^1H$-observe, $^{13}C$ double resonance probe or a $^1H$-observe, $^{13}C/^{15}N$ triple resonance probe. Software suitable for generating trial binding poses include, but are not limited to, DOCK (Ewing et al., (2001) *J. Comp-Aided Mol. Design* 15:411-428) and X-PLOR (Brünger, (1992) *X-PLOR (Version 3.1) Manual*, Yale Univ. Press, New Haven, Conn.).

Software suitable for processing and analyzing experimental NMR data is commercially available and includes, but is not limited to, FELIX (Accelrys, San Diego, Calif.), a modified version of the FELIX program (Hare Research, Inc., Woodinville, Wash.). FELIX and other processing software can be implemented on a IRIS, INDIGO workstation (Silicon Graphics, San Diego, Calif.), on a SPARC workstation (SUN Microsystems, Santa Clara, Calif.), or on IBM compatible PCs.

Figure 8:
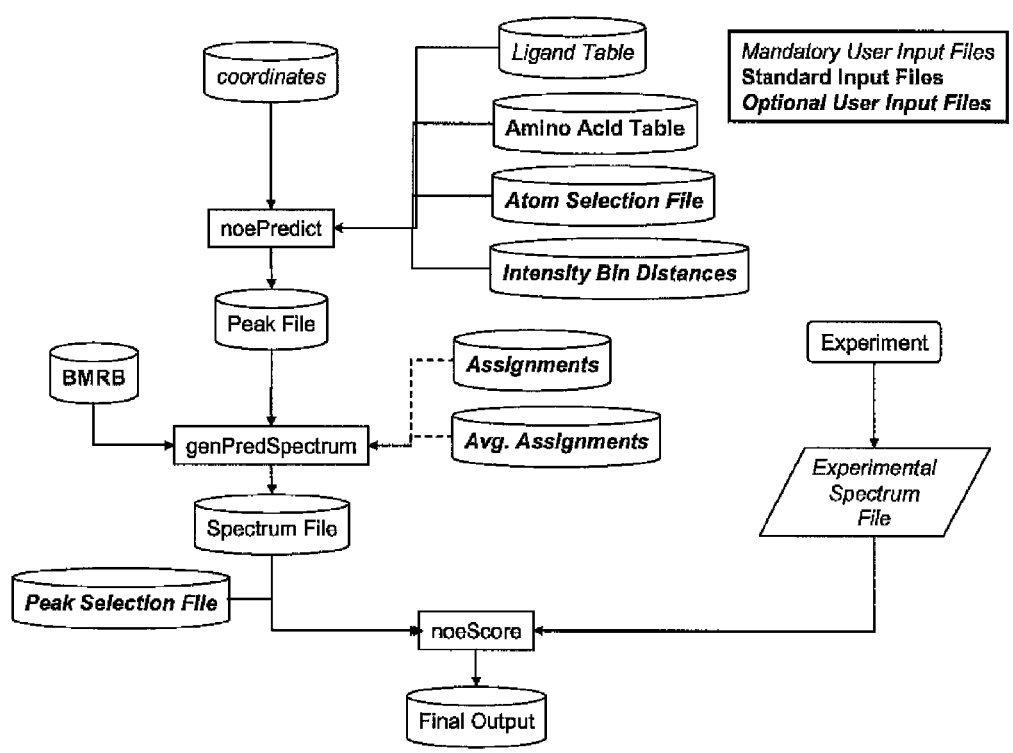
FIG. 8 is a flowchart depicting processes involved in one embodiment of the present invention; computer programs have been written to automate several of these processes.

Using standard computing tools, software for predicting spectra for trial binding poses, and for matching and scoring the predicted and observed spectra can be readily prepared using the present disclosure as a guide. FIG. 8 depicts a flowchart summarizing the processes involved in one embodiment of the present invention. Thus, FIG. 8 can be used as a guide in the coding of a suitable computer program.

IV. General Description of the Method

Strictly for purposes of illustration, each of the above described assumptions has been made in the following general description of the method. The following description is presented as a broad overview of the invention. Further, as noted herein, atoms and equivalent groups of atoms are referred to as atoms or groups, unless noted otherwise or unless context indicates otherwise.

IV.A. Treatment of Experimentally-Observed Peaks

Each of the resolved, assigned ligand atoms has an associated F3 plane in the observed 3D spectrum. The total set of experimentally observed peaks over all F3 planes can be denoted $\{EPK_m\}$; m=1, ... NEPK, Each of these experimental peaks has associated experimental $^1H$ and $^{13}C$ chemical shifts from the protein, denoted $H1EPK_m$ and $C13EPK_m$, respectively. The experimental peaks can be "unaliased" in F2, either using heuristic rules, or by recording unaliased spectra. In one embodiment, "unaliasing" is done using heuristic rules prior to subsequent analysis, in other embodiments unaliasing can be done by additional experimental means. As used herein, the term "unaliased" means to determine the actual unaltered $^{13}C$ resonance position that would be obtained for a given peak if the actual unaltered $^{13}C$ resonance position were within the $^{13}C$ frequency range sampled in the F2 dimension of the 3D $^{13}C$-edited, $^{15}N/^{13}C$-filtered NOESY experiment. Each experimental peak also has an associated experimental intensity, denoted $IEPK_m$. These intensities can be assigned to arbitrary integer values representative of peak intensity, for example 4 for a very strong peak, 3 for a strong peak, 2 for a medium peak, and 1 for a weak peak.

In general, more than one ligand atom can have NOE interactions with a particular target protein atom, and vice versa. Therefore, the experimental peaks can clustered between, but not within, F3 planes based on their $^1H$ and $^{13}C$ chemical shifts, and possibly additional optional criteria, to produce a set of protein $^1H^{13}C$ groups with possible experimental protein assignments $\{EAS_k\}$; k=1, ... NEAS. Each of these possible experimental assignments has associated chemical shifts $H1EAS_k$ and $C13EAS_k$.

IV.B. Theoretically-Determined (Predicted) Peaks

Each of the resolved, assigned ligand atoms has a list of theoretical peaks predicted for each of one or more sampled binding modes. For a given binding mode, the entire set of theoretical peaks can be denoted as $\{TPK_n\}$; n=1, ... NTPK. The theoretical peaks are restricted to include only atoms in $\{PAT_i\}$, and to be within a given intermolecular distance cutoff; this cutoff is described further herein. Each of these theoretical peaks has associated theoretical $^1H$ and $^{13}C$ chemical shifts from the protein, $H1TPK_n$ and $C13TPK_n$, respectively, along with uncertainties $\sigma H_n$ and $\sigma C_n$.

The theoretical protein chemical shifts and uncertainties can be derived in various ways. For example, some of the protein binding site residues may already be assigned. In this case, the actual shifts and appropriately small uncertainties are used throughout the calculations. In another example, throughout the calculation the average chemical shifts and standard deviations available from the Biological Magnetic Resonance Data Bank (BMRB) can be used for unassigned protein atoms or groups. In yet another example, chemical shifts for the target protein, with the target protein being taken as isolated and without any contributions from the ligand, can be computed using a computer program, such as SHIFTS (Sitkoff & Case, (1997) *J. Am. Chem. Soc.* 119:12262-73; Xu & Case, (2001) *J. Biomolec. NMR* 21:321-33), and used in the calculation. In still a further example, theoretical protein chemical shifts and uncertainties are computed for each sampled binding mode, using, for example, a parameter-based shift program modified to handle non-peptide ligands.

Each theoretical peak can be associated with an estimated intensity $ITPK_n$. As with the experimental intensities, these intensities can be expressed as integer classes. These theoretical peak intensity classes are based on intermolecular distances derived for a given binding mode. For example, intensities can be described as very strong (intensity I=4) for r<2.7 Å, strong (I=3) for 2.7 Å≦r<3.5 Å, medium (I=2) for 3.5 Å≦r<4.5 Å, and weak (I=1) for 4.5 Å≦r<5.5 Å. In this example, distances greater than 5.5 Å are not expected to give rise to an NOE signal. These cutoffs can be adjusted so that average number of peaks predicted for each pose reasonably approximates the number of peaks observed experimentally. This approach simplifies intensity normalization, and is consistent with semi-quantitative NOE distance information. Theoretical peaks are obtained for the subset of $\{PAT_i\}$ within a specified cutoff distance (e.g. 5.5 Å). Also, equivalent groups of protons (methyls and symmetric aromatic ring protons) are defined for both the protein and the ligand for the distance calculations, since the "effective distance" r of the NOE interaction is given by $(\Sigma r^{-6})^{-1/6}$; thus, there are nine terms in this sum for a methyl-methyl NOE. At this point in the general description, sets of experimental and theoretical peaks are available for each of the resolved, assigned ligand atoms $LAT_j$ for a given binding mode. The mapping between the theoretical and experimental peaks that produces the best score (lowest cost) for a given binding mode can then be determined using these peaks.

IV.C. Determining a Score (Cost)

The predicted theoretical peaks are associated with specific protein atom assignments, whereas the experimental peaks need not be. Both experimental and theoretical peaks are associated with specific ligand atoms. For a given binding mode, a set of all of the protein groups that give rise to predicted NOEs to one or more ligand atoms is constructed. This provides a set of theoretical assignments for those groups predicted to be involved in NOEs, based on the selected binding mode. This set, which is a subset of $\{PAT_i\}$, can be denoted $\{TAS_q\}$; q=1, . . . NTAS. Each of these protein groups has associated predicted chemical shifts $H1TAS_q$ and $C13TAS_q$ and associated uncertainties, which are mapped to the theoretical peak uncertainties. Some of these predicted shifts and uncertainties can be experimentally-observed values, if appropriate sequence-specific protein assignments are available.

Continuing, each of the experimentally-observed $^1H$, $^{13}C$ shifts in $\{EAS_k\}$, which are derived from the peaks observed in the NOESY spectrum, e.g., a 3D $^{13}C$-edited, $^{15}N/^{13}C$-filtered NOESY spectrum, is then mapped to one of the nuclei or groups in $\{TAS_q\}$, and a score is computed for this mapping. This procedure reduces the problem of mapping observed peaks to predicted peaks to one of mapping observed protein $^1H^{13}C$ groups (which can be identified by clustering the experimentally observed peaks) to protein $^1H^{13}C$ groups predicted to give rise to intermolecular NOE on the bases of the pose. A brute-force exhaustive search for the optimal mapping is, in general, not feasible due to a potentially vast number of possible mappings, resulting in a combinatorial explosion. Therefore, a directed search strategy is preferably employed.

Figure 2:
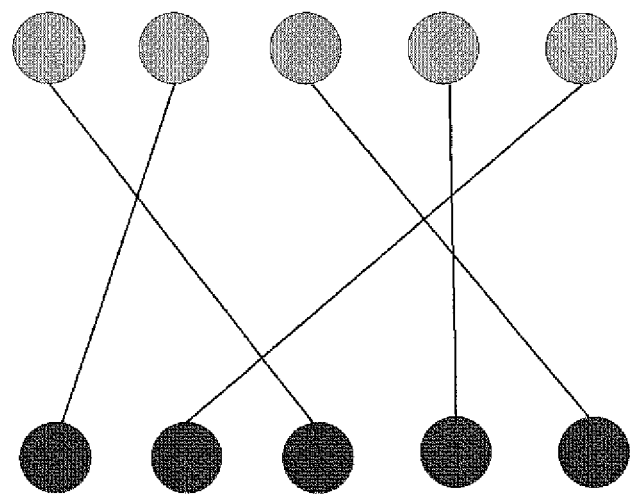
FIG. 2 is a diagram depicting a completely matched bipartite graph with N=5.

In one aspect of the present invention, the mapping problem can be cast as an equally partitioned bipartite graph weighted matching problem (Papadimitriou and Steiglitz, (1982) *Combinatorial Optimization*, Dover, Mineola, N.Y.), which is a combinatorial optimization problem that can be solved by deterministic algorithms that are $O(N^3)$ in complexity (Papadimitriou and Steiglitz, (1982) *Combinatorial Optimization*, Dover, Mineola, N.Y.; Carpaneto et al., (1995) *ACM Trans. Math. Software* 21:394-409). An equally partitioned bipartite graph is a graph whose nodes are partitioned into two subsets, each containing N nodes. An example of a completely connected bipartite graph is shown in FIG. 1. In a completely connected bipartite graph, each node i in one subset is connected by an edge to each node j in the other subset; there are no edges between nodes in the same subset. Each edge is associated with a cost C(i,j); these costs define the N*N cost matrix. A matching of a graph is a subset of edges with the property that no two edges share the same node. For an equally partitioned bipartite graph, a complete matching is a matching with N edges, as shown in FIG. 2. The algorithms referenced above find the optimal complete matching, which is the permutation that minimizes the total cost of the complete matching. Recently, combinatorial optimization has been used to assign protein backbone resonances (Hus et al., (2002) *J. Magn. Reson. B* 108:176-84; Xu et al., (2002) *Comput. Sci. Eng.* 4:50-62), but not to study protein-ligand interactions.

Using the optimization approach described, a mapping between $EAS_k$ and $TAS_q$ can be developed. Sometimes NEAS does not equal NTAS, and the matching algorithms require equal partitioning. One solution, however, is to map the experimental and theoretical $^1H$,$^{13}C$ assignment pairs to "unassigned" nodes. In this approach, unassigned nodes (designated as U nodes) can be added to make the number of elements in $EAS_k$ equal the number of elements in $TAS_q$, and to ensure that all nodes containing peaks (designated as P nodes) can be mapped to unassigned nodes.

Figure 3:
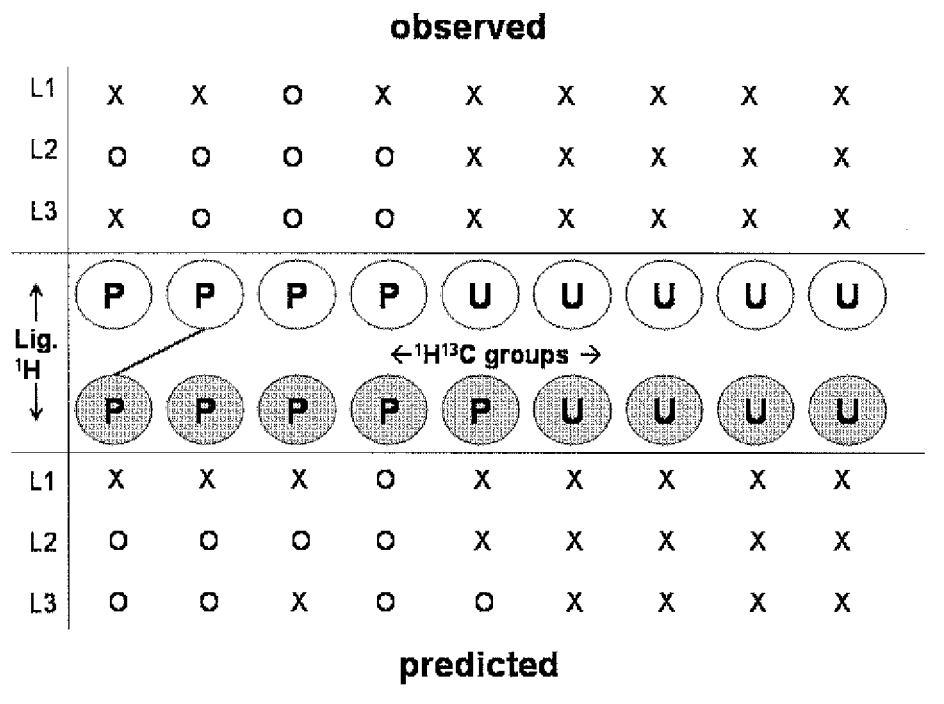

For example, if NEAS=4 and NTAS=5, 5 U nodes can be added to $EAS_k$ and 4 U nodes can be added to $TAS_q$ to yield N=9, as shown in FIG. 3. In this example, N=9. Three ligand protons (NLAT=3) give rise to observable NOEs. Observed or predicted peaks are represented by "O", and missing peaks are represented by "X" in FIG. 3. There are 4 experimental $^1H/^{13}C$ protein assignment pairs (NEAS=4) that are each associated with one more peaks in the experimental spectrum. These nodes are represented by circles designated "P." In total, 8 experimental peaks are observed (NEPK=8). Experimental unassigned nodes are represented by circles designated "U." There are 5 theoretical $^1H/^{13}C$ protein assignment pairs (NTAS=5) that are each associated with one more peaks in the predicted spectrum. These nodes are represented by circles designated "P". In total, 9 theoretical peaks are observed (NTPK=9). Theoretical unassigned nodes are represented by circles designated "U" in FIG. 3. One possible edge between the experimental and theoretical $^1H/^{13}C$ protein assignment pairs is shown.

In designing a cost function, it is preferable to account for experimental peaks that are not predicted, and for predicted peaks that are not observed. Also, it is preferable to give more weight to the experimental peaks than to the theoretical peaks, since there are experimental factors that can lead to attenuation of NOE peaks. Similarly, it is also preferable to give more weight to strong peaks.

IV.D. Determining a Cost Function

Combinatorial optimization produces a mapping between $\{TAS_q\}$ and $\{EAS_k\}$. All of the assignments in $\{TAS_q\}$ map to one more peaks in $\{TPK_n\}$, and all of the assignments in $\{EAS_k\}$ map to one or more peaks in $\{EPK_m\}$. The elements of the asymmetric N*N cost matrix are given by:

$$C(k, q) = \sum_i M_i(k, q); i = 1, NLAT \quad (1)$$

Referring to FIG. 3 and simplifying the notation, the matching cost M between an experimental peak and a theoretical peak is defined by the following expressions:

$M_i(X,X)=0$; (no exp. peak, no theo. peak) (2)

$M_i(O,X)=K_1(IE_i)^2$; (exp. peak present, no theo. peak) (3)

$M_i(X,O)=K_2(IT_i)^2$; (no exp. peak, theo. peak present) (4)

$M_i(O,O)$: (exp. peak present, theo. peak present) (5)

Employing the definitions and expressions provided herein, the following routine is developed:

```
If IE > IT, then
    M(O,O) = K_H(ΔH1/σH)² + K_C(ΔC13/σC)² + K_3(ΔI)²
Else
    M(O,O) = K_H(ΔH1/σH)² + K_C(ΔC13/σC)² + K_4(ΔI)²
End If
```

The Ks are adjustable parameters that are adjusted to obtain a suitable balance between $^1H$ chemical shifts, $^{13}C$ chemical shifts, and intensity classes. More weight is given to experimental peak intensities relative to theoretical peak intensities. The default set of parameters is $K_H=1$, $K_C=1$, $K_1=12$, $K_2=6$, $K_3=3$, $K_4=1$. The terms containing chemical shifts in equation 5 are not written out fully; they are implemented as harmonic square well functions (see, e.g., Constantine et al., (1995) *J. Magn. Reson. B* 108:176-84) so that the cost is 0 within specified bounds.

The optimal solution of the complete matching problem is a permutation π of $\{1, 2, \ldots, N\}$ that minimizes. Therefore, an algorithm that can be employed in the methods is $$COST_{mode} = \sum_k C(k, \pi(k)); k = 1, N \quad (6)$$

In pseudocode, one possible embodiment of the algorithm is described as:

```
"Unalias" experimental peaks;
Read initial protein coordinates;
Read ligand atom/equivalent group definitions;
Read in {PAT_i};
```

```
Read protein assignments, uncertainties and restraints, if any;
Read experimental peaks (F1 shift, F2 shift, I class, F3 assignment)
→ {EPK_m};
    Cluster experimental peaks to produce {EAS_k};
    Produce and loop over selected binding modes:
        Compute {TPK_n} using distances, predicted shifts or
            experimental shift assignments (if any);
        Compute {TAS_q};
        Compute cost matrix C(k,q) and optimal mapping between
            {TAS_q} and {EAS_k};
        Store COST_mode and additional data;
    End loop over binding modes;
    Save data on binding modes, including mappings and assignments.
```

As described in the Examples presented herein, the described procedures have been employed using both synthetic and real data sets.

Figure 5:
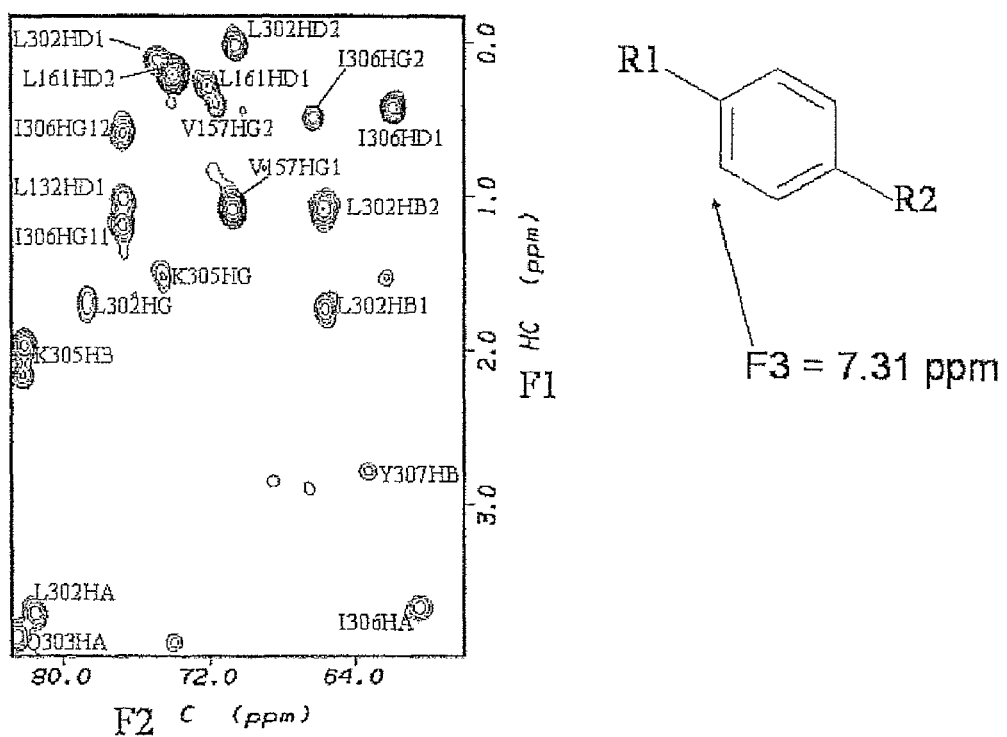
FIG. 5 is an example 2D plane (F1, F2) from a 3D $^{13}C$-edited, $^{15}N/^{13}C$-filtered HSQC-NOESY experiment recorded using a sample of LFA1 I-domain complexed with Compound 1. All of the NOEs shown involve the equivalent ligand protons at 7.31 ppm (F3). Peaks are labeled with their assigned protein $^1H$ resonances (F1). The attached $^{13}C$ resonance position is displayed along F2.

One embodiment of the present invention employs data derived from a single 3D $^{13}C$-edited, $^{15}N/^{13}C$-filtered HSQC-NOESY experiment recorded using a uniformly $^{13}C/^{15}N$-labeled protein sample; however, it is noted that the method has also been adapted to other types of protein isotopic labeling schemes and other types of protein-ligand NOE experimental data (e.g., 2D $^1H$-$^1H$ NOE data obtained using residue type-specific labeling of protein samples) by suitable modifications of the computational procedures. For example, if a series of protein samples are prepared in which specific residues types are $^1H$ and/or $^1H$,$^{13}C$-labeled, with all other residues being $^2H$-labeled, only those protons that are actually present in one or more of the samples are included when predicting NOE interactions for trial ligand binding poses. This is accomplished by use of an "atom selection" input file. In addition, equation 5 has been modified to ensure that a group of experimental peaks arising from a known set of residue types is heavily penalized unless it is matched to a predicted group of predicted peaks that arise from the same known set of residue types. More generally, the procedure in its current embodiment is able to utilize data involving many possible isotopic labeling schemes. It may be possible to restrict the assignment of an experimental $^1H$ or $^1H/^{13}C$ group to a restricted set of possible residue types (as described herein), to specific residue locations in the protein sequence, or to specific atom types within residues. Mappings between experimental P-nodes and theoretical P-nodes (as shown in FIG. 5) are penalized heavily if they do not comply with information provided in a "peak specification" input file. If certain residue and/or atom types can be excluded all together (e.g, because they are $^2H$-labeled in all samples), they can be excluded from PATi (through use of the "atom selection" file) prior to calculation of the predicted spectrum.

The process of determining a cost associated with a given pose can be repeated for each member of an ensemble of binding poses. For example, the general process of selecting a pose, predicting a theoretical NMR spectrum and assigning a cost value to the pose can be repeated for each member of an ensemble to create a collection of cost values.

IV.E. Determining the Optimal Ligand Pose

Once costs have been calculated for each trial pose, the costs can be compared to each other and a determination made as to which pose or set of poses represents the closest match to the experimental data. Typically this will be those with relatively low cost values.

V. Specific Embodiment of the Method

Having provided a general overview of the present invention, a description of a particular embodiment of the invention is presented. As described herein, in one embodiment, the present invention comprises a method of determining a preferred binding pose of a ligand in a complex comprising a target protein and a ligand of interest using non-scalar magnetic couplings. An advantage of the present invention is that the invention does not require the assignment of NMR peaks that arise from protein nuclei. This ability allows intermolecular protein-ligand non-scalar couplings to be used for ligand binding pose determination much more completely and rapidly than is now possible. The present invention also facilitates in silico efforts to optimize the protein-binding properties ligands. It is noted that the following description of an embodiment of the invention is presented in a particular order of steps, but this is purely for purposes of explanation. Unless explicitly or implicitly indicated otherwise, the steps need not be followed in the order presented below; rather, the order of steps can be adapted to suit a particular application of the invention.

It is noted that spectrum acquisition and processing in all embodiments of the present invention can be carried out using commercially-available NMR hardware and software packages, the identities which will be known to those of ordinary skill in the art and may be in addition to those materials described herein. There is no requirement that the method employ a magnet of any particular field strength, although it is generally preferable to employ a high field. Similarly, there is no requirement on the software package used to control acquisition or processing of acquired data. Some examples of hardware and software packages that can be employed in the present invention are presented herein.

In one embodiment of the present invention, the NMR resonance shifts of a ligand of interest are assigned first. Although the present invention eliminates the need to assign specific protein resonances, the ligand's resonances should be assigned. Unlike assigning protein resonance, however, it is often a relatively straightforward procedure to assign the resonances of a small molecule bound to a protein, or exchanging between free and bound states. An NMR spectrum of the ligand can be acquired using standard NMR techniques and the assignments of the peaks can be made either manually or employing appropriate software, as described herein. In some cases, ligand resonances can be assigned using a one-dimensional NMR experiment; however, in general it may be desirable to employ a two-dimensional isotope-filtered NMR experiments to assign resonances, in which case 2D F1/F2-$^{13}$C/$^{15}$N-filtered HSQC-NOESY, TOCSY and/or COSY spectra can be acquired. Alternatively, bound or exchanging ligand resonances can be assigned by recording standard 2D $^1$H-$^1$H through-bond and through-space correlation spectra utilizing a sample in which the protein is fully $^2$H-labeled.

An observed NMR peak pattern comprising the target protein resonances and ligand resonances can then be acquired. The observed peak pattern indicates non-scalar couplings between the nuclei of a sample comprising a target protein and a ligand. The observed NMR peak pattern can comprise experimentally-determined data, or (for algorithm testing purposes) it can comprise non-experimentally determined data (e.g., for algorithm testing purposes). One NMR experiment that can be employed to acquire experimentally-determined data is a three-dimensional $^{13}$C-edited, $^{15}$N/$^{13}$C-filtered HSQC-NOESY experiment. For example, estimates (of varying degrees of accuracy) can be obtained for the predicted values of the target protein resonances in a variety of different ways. In one embodiment, the target protein resonances are obtained by estimating target protein resonance shifts from pre-existing data, such as those available in the BMRB, or from previously assigned protein-ligand complexes with similarity to the complex under study. Alternatively, the target protein resonance shifts can be predicted in silico. These options for acquiring target protein resonances can be employed in conjunction with, or in exclusion to, experimentally determining target protein resonance shifts. The observed NMR peak pattern will feature contributions from both the target protein and the ligand. In this regard, some or all of the ligand population is bound to the target protein; this association with the protein can be in either a fast-exchanging or slow-exchanging equilibrium.

In one aspect of the present invention, rather than mapping individual predicted peaks to individual observed peaks, the present invention produces a mapping between $^1$H$^{13}$C groups predicted to be involved in intermolecular NOEs with $^1$H$^{13}$C groups observed to be involved in intermolecular NOEs. This procedure greatly reduces the size of the mapping problem; furthermore; it insures that the predicted mappings, and hence predicted peak-atom assignments, are self consistent; i.e., observed peaks with different protein chemical shifts cannot be mapped to the same protein $^1$H$^{13}$C group predicted by a given pose, since such peaks are placed in different experimentally observed $^1$H$^{13}$C groups, and must be mapped to different predicted $^1$H$^{13}$C groups. If peak-to-peak mapping were employed, such inconsistencies could arise.

As with all spectra acquired in the course of practicing the present invention, the spectrum can be acquired using standard NMR pulse sequences and methodologies. It is noted that for purposes of the present invention, "non-scalar couplings between nuclei" include any and all couplings arising from through-space, as opposed to scalar "through-bond," transfer of magnetism, although scalar connectivities can be employed in a filtering role.

Trial ligand binding poses for the ligand can then be generated. The trial poses can be generated by performing an in silico operation to define an orientation and conformation of the ligand at a selected location relative to one or more three-dimensional structures of all or a portion of the target protein. There are many software packages available that can facilitate the in silico generation of a trial ligand binding pose. Representative examples of such software packages include DOCK (Ewing et al., (2001) *J. Comp-Aided Mol. Design* 15:411-428) and X-PLOR (Brünger, (1992) *X-PLOR (Version 3.1) Manual*, Yale Univ. Press, New Haven, Conn.). In some embodiments, the in silico operation can comprise modeling the ligand and/or performing a docking operation to dock the ligand, in its trial binding pose, with the target protein. When an in silico approach is employed, experimentally-derived data can be employed in the method, such as data derived from an NMR spectrum. Experimentally-derived data can be employed alone or in conjunction with a modeling operation or a docking procedure.

Continuing, an NMR peak pattern of the target protein and the ligand in its assigned trial binding pose can be predicted. The predicted NMR peak pattern represents a peak pattern or spectrum that would be expected to be observed if the ligand, which has been assigned a particular binding pose, and the target protein were contacted with each other in vitro, and an NMR spectrum acquired. In one embodiment, the step of acquiring a predicted NMR peak pattern comprises the steps of (a) obtaining target protein NMR resonance shifts; (b) obtaining and assigning target ligand NMR resonance shifts (c) selecting a target protein nucleus and a ligand nucleus to form a protein-ligand pair; (d) predicting the peak intensity of a proposed magnetic interaction between each member of the pair; (e) predicting peak shifts for the proposed magnetic interaction between each member of the pair; (f) placing each predicted peak in a pattern, the predicted peak being representative of the predicted peak intensity and predicted peak shift; and (g) repeating steps (c) through (f) for each of a selected number of protein-ligand pairs.

As described herein above, target protein NMR resonance shifts can be obtained by estimating target protein resonance shifts, predicting target protein resonance shifts in silico, experimentally determining target protein resonance shifts, or a combination of one or more of these approaches. When target protein NMR resonance shifts are obtained experimentally, they can be obtained using well-established procedures (e.g. Metzler et al., (1996) *Biochem.* 35:6201-6211). Ligand assignments can be obtained by determining the bound or exchanging ligand $^1$H shifts by employing data obtained from two-dimensional (2D) double-$^{15}$N/$^{13}$C-filtered through-bond and through-space correlated. NMR experiments, or by using standard 2D $^1$H-$^1$H through-bond and through-space correlated NMR experiments in conjunction with a fully $^2$H-labeled protein sample.

Stated generally, the step of predicting an NMR peak pattern generally involves selecting a ligand nucleus and determining which target protein nuclei could magnetically interact with the selected ligand nucleus. Thus, a selected ligand nucleus is paired with a selected target protein nucleus and an assessment of whether the pair could give rise to a magnetic interaction is made. The assessment can involve an evaluation of a variety of physical phenomena, such as the spatial distance between the members of the pair and the local magnetic environments of the respective nuclei.

More specifically, the step of predicting possible non-scalar magnetic interactions can involve (a) predicting the peak intensity of a proposed magnetic interaction between each member of a pair of selected nuclei, and (b) predicting peak shifts for the selected groups of protein nuclei. In the simplest approximation, peak intensities are a simple function of the distance between the two nuclei, and in the prediction can be assigned an integer value based on distance, with higher values corresponding to shorter distances and lower values corresponding to longer distances. A particular cutoff value can be selected, which represents the intermolecular distance at which point no through-space transfer of magnetism occurs. For example, if a cutoff value of 5 Å is selected, nuclei that are spatially farther than 5 Å from one another will not generate a peak. Integer values can be arbitrarily assigned to intensities based on distance, with shorter distances having higher value. For example, nuclei that are <2.5 Å apart could be assigned a value of 4; nuclei between 2.5 and 3.0 Å apart could be assigned a value of 3; nuclei between 3.0 and 4.0 Å apart could be assigned a value of 2, and nuclei between 4.0 and 5.0 Å apart could be assigned a value of 1. Nuclei greater than 5 Å apart would not be expected to give rise to a peak and can be assigned an intensity value of 0.

Peak shifts are a function of the of the local magnetic environment of the two nuclei. The peak shifts of the selected nuclei, therefore, can be predicted based on an evaluation of the local magnetic environment. For example, peak shifts can be estimated by querying a database, such as the BMRB, and extracting peak shifts therefrom, by employing an algorithm for chemical shift prediction (e.g., SHIFTS (Sitkoff & Case, (1997) *J. Am. Chem. Soc.* 119:12262-73; Xu & Case, (2001) *J. Biomolec. NMR* 21:321-33), or by employing experimentally-generated results. Experimentally-generated results can be employed in a variety of ways and can include data on a protein or protein/ligand complex that is similar, but not identical, to the protein-ligand complex in question.

After predicted peak shifts and peak intensities are generated, each predicted peak can be placed in a pattern, the predicted peak being representative of the predicted peak intensity and predicted peak shift. Peaks with a predicted intensity of zero are omitted, as they represent interactions between nuclei that would be too spatially distant for a transfer of magnetism to occur.

After placing a predicted peak in a pattern, the process of selecting another pair of nuclei can be performed again and ultimately another peak placed in the pattern. By building up the pattern by considering all or a significant number, of possible nucleus pairs, a predicted spectrum can be generated that represents all possible interactions between all combinations of protein and ligand nuclei. This pattern is a predicted peak pattern and can subsequently be compared with an observed peak pattern, as described herein.

The present invention can be applied to individual nuclei or it can be applied to groups of magnetically-similar nuclei. That is, magnetically-similar nuclei can be grouped together and a given predicted peak can be attributed to, or predicted to arise from, the interaction between one nucleus or a group of magnetically-similar nuclei and another one or a group of magnetically-similar nuclei.

Summarily, the step of predicting possible non-scalar magnetic interactions can include factors that account for the shift and intensity of a magnetic interaction between a pair of selected ligand-protein nuclei, a pair comprising a selected ligand nucleus and a group of magnetically-similar target protein nuclei, a pair comprising a group of magnetically-similar ligand nuclei and a target protein nucleus, and a pair comprising a group of magnetically-similar ligand nuclei and a group of magnetically-similar target protein nuclei. The pairs can be evaluated to determine if a magnetic interaction between the pair would generate a peak and if so, a peak that reflects the intensity and chemical shift of the interaction can be placed in the predicted spectrum. The predicted spectrum can comprise one or more predicted peaks.

The predicted peak pattern can then be compared with the observed peak pattern. This comparison provides an indication of the degree of similarity between the observed and predicted peak patterns. The comparison can take any form that provides a indication of the similarities and differences between the observed peak pattern and the predicted peak pattern. In one embodiment, the comparing (a) arranging into an equally partitioned bipartite graph groups of protein nuclei observed to give rise to intermolecular non-scalar magnetic couplings and groups of protein nuclei predicted to give rise to intermolecular non-scalar magnetic couplings, wherein the protein groups observed to produce intermolecular non-scalar magnetic couplings are placed in a first subset of nodes, and the protein groups predicted to produce intermolecular non-scalar magnetic couplings placed in a second subset of nodes; and (b) mapping the first subset of nodes to the second subset of nodes. Note is taken of those nodes which completely map and those that do not completely map.

In one embodiment, the mapping problem is cast an equally partitioned bipartite graph weighted matching problem (Papadimitriou and Steiglitz, (1982) *Combinatorial Optimization*, Dover, Mineola, N.Y.), which is a combinatorial optimization problem that can be solved deterministically. One specific algorithm, the "Hungarian method", solves the matching problem of the bipartite graph in $O(N^3)$ arithmetic operations (Papadimitriou and Steiglitz, (1982) *Combinatorial Optimization*, Dover, Mineola, N.Y.; Carpaneto et al., (1995) *ACM Trans. Math. Software* 21:394-409). This algorithm finds the optimal complete matching, which is the permutation that minimizes the total cost of the complete matching.

After comparing the observed and predicted peak patterns, the trial binding pose is assigned a quantitative score representing the degree of similarity between the observed and theoretical peak patterns. This can be achieved by defining a quantitative score for the optimal complete matching between the node subsets, based on an evaluation of deviations between observed and predicted peak patterns. The quantitative score can be a relative score and can be assigned based on an arbitrarily established scale, with the proviso that the same scale be used for all members of an ensemble of trial binding poses. This proviso is met by simply utilizing the same parameter values in the definition of the cost matrix (equations 1-6) when scoring and comparing trial poses. If the observed and predicted peak patterns match with exactly the same number of peaks, grouped exactly the same way, and with all observed chemical shifts and intensities matching all of the predicted chemical shifts and intensities within their specified uncertainties, the total cost of the complete matching will be 0. Otherwise, the cost will increase with increasing differences in the overall pattern of peaks observed, and with increasing differences between the observed and predicted chemical shifts and intensities between matched peaks.

The collective procedure of designating a trial binding pose, predicting a peak pattern of the target protein and the ligand in its assigned trial binding pose, comparing the predicted peak pattern with the observed peak pattern, and assigning the trial binding pose a quantitative score representing the degree of similarity between the observed and theoretical peak patterns based on the comparison can be repeated a desired number of times to generate a quantitative score for each of one or more binding poses. In practice, a trial binding pose can be designated, a predicted peak pattern representing the non-scalar magnetic interactions between the ligand in its designated binding pose and the target protein can then be generated and the predicted peak pattern compared with the observed peak pattern. The degree of correlation between the observed and predicted peak patterns is then analyzed and on the basis of that analysis/comparison, the ligand binding pose is assigned a quantitative score. By repeating this procedure for each of one or more ligand binding poses, a collection of quantitative values representing the "goodness of fit" between the observed and predicted peak patterns is generated. Generally, it is desirable to perform the procedure on a large number of trial binding poses, since a larger number of possible trial poses statistically increases the likelihood that the optimal trial binding pose is representative of the real world binding event, although such an ensemble can comprise any number of trial ligand binding poses.

Once an ensemble of quantitative scores is generated, an evaluation of the assigned quantitative scores can be made and the one or more binding poses that are the most consistent with the observed peak pattern can be identified. In addition, the use of bipartite matching to explicitly match observed and predicted $^1H^{13}C$ groups giving rise to peaks affords trial assignments for the experimentally observed $^1H^{13}C$ groups. In cases where the experimental assignment is known, this provides a means of testing the ability of the algorithm to produce correct $^1H^{13}C$ group assignments, in addition to its ability to identify the correct binding pose. In cases where the experimental assignments are not known, the algorithm provides trial assignments. These trial assignments can be assigned a confidence value based on their frequency of occurrence in the low cost binding poses. Those trial assignments with high confidence can be used to derive explicit restraints for a subsequent round of pose generation and evaluation, yielding an iterative refinement process. Such an iterative process is not possible with any similarity measure between the observed and predicted spectra that does not provide trial $^1H^{13}C$ group assignments.

VI. Other Embodiments of the Present Invention

Those of ordinary skill in the art will recognize that the fundamental procedures of the present invention can be modified in a variety of ways without departing from the scope of the invention. By way of example, several representative, but non-limiting examples of possible extensions and embodiments of the present invention are presented.

VI.A. Additional Explicit Restraints

The search space can be greatly restricted if explicit restraints are incorporated into a docking operation. In addition to inter-proton distance restraints (both intra- and inter-molecular), these restraints can include dihedral angle restraints and dipolar coupling restraints. The latter can involve defining inter-nuclear vectors with respect to an "alignment tensor."

VI.B. "Missing" Experimental Peaks

It is sometimes the case that peaks expected to be observed in an NMR experiment are absent. In one aspect of the present invention, this case is has been accounted for in the provided definition of the cost function, since more weight can be given to experimental peaks that are not predicted relative to predicted peaks that are not observed. Thus, in the case in which expected experimental peaks are missing, the cost function can be weighted to account for the absence of the expected peaks.

VI.C. Fast Calculation of Chemical Shifts for all Trial Binding Modes

In one embodiment, the present invention employs protein chemical shift estimates that are fixed throughout the docking and scoring steps of the procedure. It is known that ligand binding can induce chemical shift changes, due to direct interactions with protein atoms and conformational changes. Fast calculation of ligand-induced chemical shift changes for trial binding modes can account for these changes in an approximate manner, and can be desirable in some situations. To estimate these chemical shift changes, a program can be generated that can compute chemical shift parameters for general organic molecules. These parameters can then potentially be used in the rapid estimation of ligand-induced chemical shift changes.

VI.D. Peak Degeneracy

In some cases, peaks in an observed NMR spectrum will overlap one another, such that it is not possible to pick separate and distinct peaks. In cases of overlap involving assigned ligand resonances, peak overlap can be dealt with by lumping these atoms together when defining equivalent groups for the ligand.

Overlap of protein resonances can also be dealt with. If severe overlap is recognized, additional peaks can be added to the experimental peak list. In rare cases, the overlap may be so severe that it is not recognized, even by visual inspection. When this situation is identified, there are at least two ways to solve this problem. The first way is to ignore the problem and continue the analysis. Another possibility is to add a third class of nodes (duplicate or "D" nodes) to the bipartite graph (see FIG. 5) and modify the described analysis to account for these duplicate notes.

VI.E. Sets of Experimental $^1H/^{13}C$ Pairs Known to Belong to the Same Residue In some cases, it may be known that certain experimentally-observed $^1H/^{13}C$ pairs must belong to the same residue, although it may not be known to which specific residue. For example, it may be known that the peaks labeled "L302HB1" and "L302HB2" in FIG. 1 must arise from the same residue. Incorporating this information appears to present difficulties. However, it the combinatorial optimization algorithm can be altered to deal with this restriction. For example, if experimental $^1H/^{13}C$ pairs X and Y are known to belong to the same residue, it may be possible to modify the algorithm such that if experimental $^1H/^{13}C$ pair X is mapped to a theoretical $^1H/^{13}C$ pair belonging to residue Z, then experimental $^1H/^{13}C$ pair Y can only be mapped to a theoretical $^1H/^{13}C$ pair also belonging to residue Z, or to an unassigned theoretical node. This may alter the deterministic nature of the algorithm, since the complete matching arrived at may depend on the order in which the edges are established.

A second alternative is an iterative approach. This involves executing the combinatorial optimization algorithm, initially ignoring the known information. In this approach, a check for inconsistencies would be performed and, if found, the lowest-cost permutation that eliminates the inconsistencies could be the focus of a search.

In a third alternative, the nodes of the bipartite graph could be defined to represent complete scalar-coupled spin systems, rather than individual $^1H^{13}C$ groups. This would require a complete mapping of all scalar coupled spin systems; e.g., by analysis of HCCH-TOCSY data.

Finally, terms can be added directly to the $COST_{mode}$ term after execution of the combinatorial optimization algorithm to reflect inconsistencies, but this would mean that there may be an alternate permutation that has a lower overall cost. Facing a related problem, it is noted that Xu et al. were able to include sequential connectivity information in a "constrained" bipartite matching procedure (Xu et al., (2002) Comput. Sci. Eng. 4:50-62). It may be possible to incorporate this type of data using a Bayesian approach.

VI.F. Redefine Cost Function in Terms of Bayesian Probabilities

In some cases, it may be possible to redefine the cost function in terms of Bayesian probabilities. In addition to information on the binding site composition and expected chemical shift ranges, it may be possible to further restrict some specific experimental $^1H/^{13}C$ assignment pairs to more narrow ranges of possible residues, and to specific atoms within residues, based on readily observed correlations.

VI.G. Dipolar Couplings Involving Unassigned Atoms

In some cases, there may be dipolar couplings involving unassigned inter-nuclear vectors. In these cases, it may be possible to incorporate matches between predicted and observed dipolar coupling into the cost matrix. This may complicate the search procedure, since the optimal orientation with respect to the alignment tensor must also be found (Hus et al., (2002) J. Magn. Res. 157:119-123), but can lead to a satisfactory solution to the problem.

VI.H. Use Protein Assignment Probabilities to Assist Automated Side-Chain Assignments As described herein, the algorithm of the present invention generates protein assignments for the best binding mode. In some situations, it may be desirable to save some number of binding modes that give comparable scores. This information can then be used to define the probabilities that a specific experimental $^1H/^{13}C$ assignment pair is, in fact, a specific group in the protein. These probabilities can assist in efforts to automate side-chain assignments and to obtain structures using standard approaches based on explicit restraints.

VI.I. Evaluation and Rescoring of Selected Poses

As described, protein-ligand NOE matching is fast enough to apply to many thousands of trial poses. Once a smaller set of the most consistent poses are identified, additional approaches become feasible. Prediction of the absolute chemical shifts for each pose can be used to rescore selected poses. These poses can also be filtered using ligand proton chemical shift changes predicted by quantum-mechanical methods (Wang et al. (2004) J. Am. Chem. Soc. 126:11430-11432). A small set of the most consistent poses can be subject to more thorough analysis using more accurate and complete force fields and computationally intensive conformational sampling techniques (Kitchen et al. (2004) Nat. Rev. Drug Disc. 3:935-949), with the resulting poses being evaluated both by NOE matching and the theoretical binding energies.

VI.J. Iterative Structure Refinement Strategy

In addition to providing $COST_{mode}$ values, NOE matching provides possible assignments for many of the experimental $^1H^{13}C$ groups, and hence possible NOE peak assignments, for each pose. By associating likelihoods with the possible assignments, explicit restraints could be derived from those assignments with high likelihoods. These restraints could then be used to limit the search space in a subsequent round of trial pose generation. By repeating this process, an iterative pose refinement strategy is feasible.

EXAMPLES

The following Examples have been included to illustrate various exemplary modes of the invention. Certain aspects of the following Examples are described in terms of techniques and procedures found or contemplated by the inventors to work well in the practice of the invention. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed without departing from the spirit and scope of the invention.

The experimental and computational procedures used to determine well-resolved NMR ensembles in the following Examples were as follows:

LFA-1/Compound 1 and muscle fatty-acid binding protein (mFABP)/Compound 2 complexes. For both complexes, NMR experiments were carried out at 20° C. on 600 MHz Varian Inova or 600 MHz Varian Unity Plus spectrometers using 5 mm $^1$H-observe, $^{13}$C-$^{15}$N triple resonance room temperature probes equipped with either triple- or single-axis (z) pulsed field gradients. All spectra were processed with a modified version of the FELIX program (Hare Research, Inc, Woodinville, Wash.)

Recombinant, uniformly $^{13}$C/$^{15}$N-labeled LFA-1 was concentrated to 1.4 mM in buffer containing 50 mM NaPO$_4$, 2 mM MgCl$_2$, 7% D$_2$O (v/v) at pH 6.7. Recombinant, uniformly $^{13}$C/$^{15}$N-labeled mFABP was concentrated to 4.0 mM in buffer containing 25 mM NaPO$_4$, 50 mM NaCl, 1 mM EDTA, 5 mM DTT, 0.1 mM NaN$_3$, 7% D$_2$O (v/v) at pH 7.5. For both samples, aliquots of concentrated ligand stock solution (in d$_6$-DMSO) were added until complete protein saturation was achieved. Both complexes are in slow exchange, as expected based on a K$_d$ of 26 nM for LFA-1/Compound 1 and a K$_i$ of ~1 nM for mFABP/Compound 2.

For both proteins, protein resonance assignments were obtained by procedures that are similar to those described in Metzler et al., (1996) *Biochem.* 35:6201-6211, and in the Supporting Information therin. Sequential backbone atom resonance assignments were obtained by analysis of 3D triple resonance experiments. For LFA-1/Compound 1, aliphatic $^1$H and $^{13}$C side chain assignments for binding pocket residues were obtained by interactive analysis of an aliphatic 3D HCCH-TOCSY spectrum. For mFABP/Compound 2, nearly complete protein side chain assignments were obtained by interactive analysis of an aliphatic 3D HCCH-TOCSY spectrum, an aromatic 2D HCCH-TOCSY spectrum, a 2D $^1$H-$^{13}$C CT-HSQC$^{Met}$ spectrum, aromatic 2D CBHD and CBHE spectra, and 2D experiments for assigning arginine side chain guanidino groups. $^1$H resonance assignments for bound ligands were obtained from interactive analysis of 2D F$_1$,F$_2$-$^{13}$C/$^{15}$N-filtered TOCSY and NOESY experiments.

The NMR ensemble for LFA-1/Compound 1 was generated starting from an X-ray structure of LFA-1 complexed with lovastatin (PDB entry 1CQP). After removing lovastatin, the X-ray structure was modified to be consistent with our construct (183 residues, with an arginine instead of tryptophan at position 189) and fully protonated using the BUILD and HBUILD routines of X-PLOR, and it was subsequently energy minimized with XPLOR. Peaks from a 3D $^{13}$C-edited, $^{15}$N/$^{11}$C-filtered NOESY spectrum ($\tau_m$=100 ms) were used to derive 41 protein-ligand distance restraints. Compound 1 was randomly rotated and translated, and then subjected to restrained simulated annealing. Compound 1 was allowed full conformational freedom during all phases of the XPLOR simulating annealing. The 6 N-terminal residues and residues within the binding pocket of LFA-1 were allowed full conformational freedom throughout the annealing process; the remaining residues were kept rigid for all but the final energy minimization, during which the entire system was given full conformational freedom.

A full NMR-based structure determination was performed for the mFABP/Compound 2 complex. Initially, a structural ensemble of the protein alone (133 residues) was determined using NMR experiments and computational protocols. A total of 2052 intra-protein NOE distance restraints were derived from a 3D $^{15}$N-edited NOESY and 4D $^{13}$C/$^{11}$C-, $^{13}$C/$^{15}$N- and $^{15}$N/$^{15}$N-edited NOESY spectra. Backbone ($\phi$) dihedral angle restraints (67) were derived from 2D $^1$H-$^{15}$N J-modulated COSY spectra. Side chain $\chi^1$ (37) and $\chi^2$ (8) restraints were derived from a 3D HNHB spectrum, a 3D $^{13}$C-edited NOESY spectrum, and a short mixing time (14.5 ms) 3D $^{13}$C-edited $^1$H-$^1$H TOCSY spectrum. In addition, 27 hydrogen bond distance restraints were derived from preliminary models and $^1$H-$^2$H exchange data. Structures of the protein alone were computed with the DIANA program (Güntert et al., (1991) *J.*

*Mol. Biol.* 217:517-530). $^1$H assignments for bound Compound 2 were obtained from 2D F$_1$,F$_2$-$^{13}$C/$^{15}$N-filtered TOCSY and NOESY experiments. From the latter ($\tau_m$=60 ms), 1 intra-ligand distance restraint and 2 protein-ligand distance restraints (involving the hydroxyl proton of Tyr129) were derived. A 3D 13C-edited, $^{15}$N/$^{13}$C-filtered NOESY spectrum ($\tau_m$=60 ms) provided 108 protein-ligand distance restraints, and 10 protein-ligand distance restraints were obtained from the 3D $^{15}$N-edited NOESY. Simulated annealing with XPLOR, incorporating all restraints, was used to produce an ensemble of the complex.

Example 1

Figure 4:
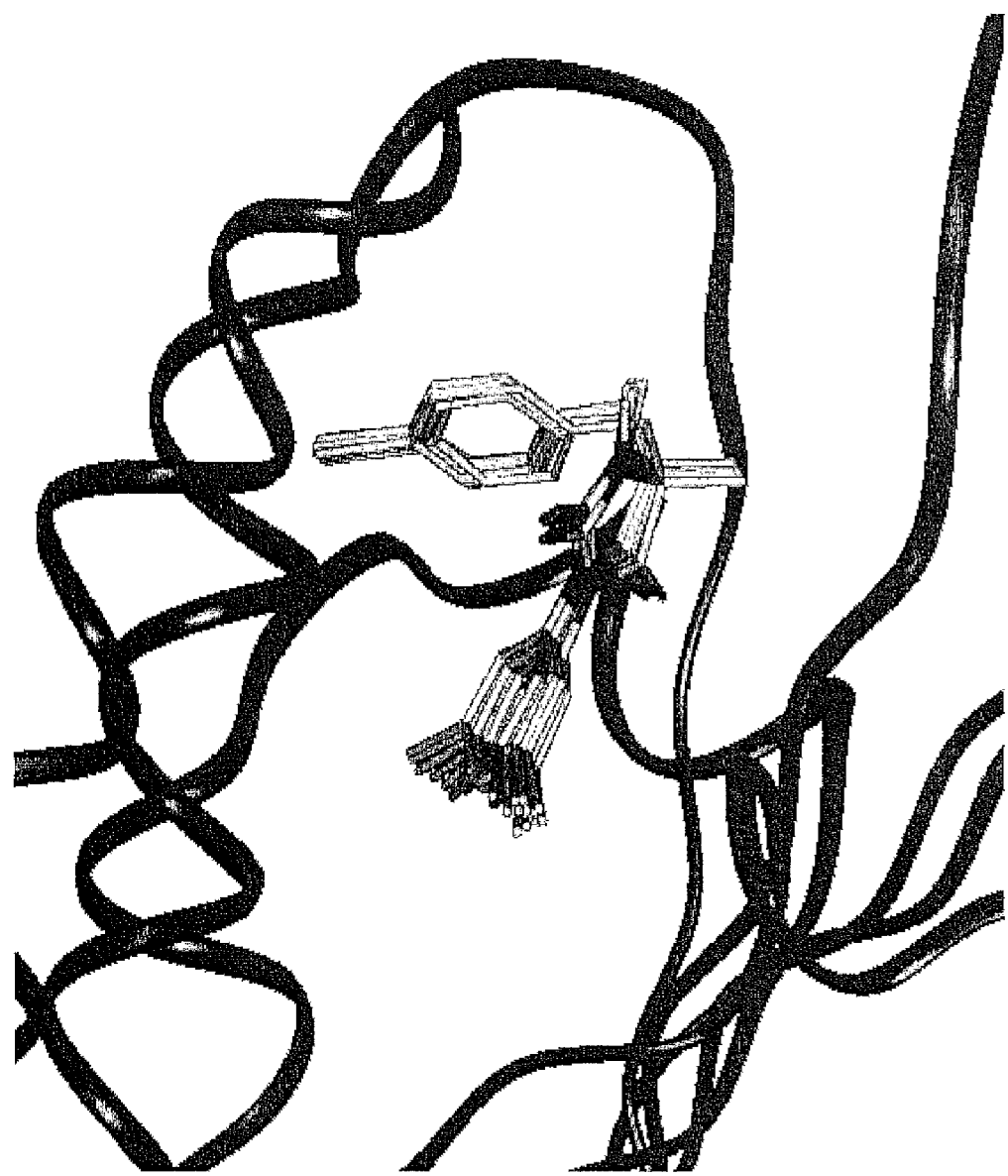
FIG. 4 is an ensemble of NMR structures depicting Compound 1 bound to LFA1 I-domain. A portion of the protein backbone is shown as a ribbon, and the Compound 1 ensemble is shown as stick diagrams.

A high-resolution NMR-derived ensemble of Compound 1 complexed with the LFA1 I-domain was acquired (FIG. 4). These structures were computed from distance restraints derived form an assigned 3D $^{13}$C-reverse-filtered NOE spectrum (FIG. 5). The structure of this complex is well defined by the NMR data, and the binding mode observed by NMR has been verified by X-ray crystal structures of highly similar compounds.

Alternate structures of the complex were generated using the software program DOCK (Ewing et al., (2001) *J. Comp-Aided Mol. Design* 15:411-428) in order to sample alternate binding modes. An additional structure was generated manually in which the binding orientation was "flipped" with respect to the experimental binding mode. One experimental structure (a representative member of the ensemble shown in FIG. 4) and the alternate structures of Compound 1 bound to LFA1 were used in test matching and scoring.

A file was prepared that contained experimental peak information, including chemical shifts, intensities and peak assignments. The observed intensities were placed into four bins. The rows in the experimental data file were ordered to cluster peaks originating from the same H/C group on the protein. This is preferably done using only chemical shift information, since some or all of the experimental assignments may not be available.

Files were also prepared that contained predicted peaks for the structures based on effective inter-proton distances. The predicted NOEs were also placed into four bins. Chemical shift information was not included with the predicted data. Instead, a copy of the latest database from the online protein NMR database BMRB (accessible via the Department of Biochemistry at University of Wisconsin-Madison webpage) was prepared that contains atom naming consistent with that used in the coordinate and assignment files. A file containing all of the experimental protein assignments was also prepared.

A program was written and used to extract chemical shifts and standard deviations from the BMRB and then combines this information with the predicted NOE intensities in order to produce complete "predicted" spectra for the structures. The program also identified peaks in the experimental data that originate from the same protein H/C group on the basis of clustering the observed $^1$H/$^{13}$C chemical shifts. In addition, the program implemented an initial version of scoring and matching using the bipartite graph matching (combinatorial optimization) algorithm.

A second protein-ligand system was also used to conduct studies: mFABP complexed with Compound 2. A high-resolution NMR ensemble of this protein-ligand complex is has been determined, and a X-ray structure of Compound 2 bound to the mFABP homolog adipocyte lipid-binding protein was determined The NOE matching and scoring algorithm described above was applied to the NMR ensemble of the mFABP/Compound 2 complex, an NMR ensemble computed with a reduced restraint set, and poses were generated using DOCK.

Figures 6A, 6B, 6C, 6D:
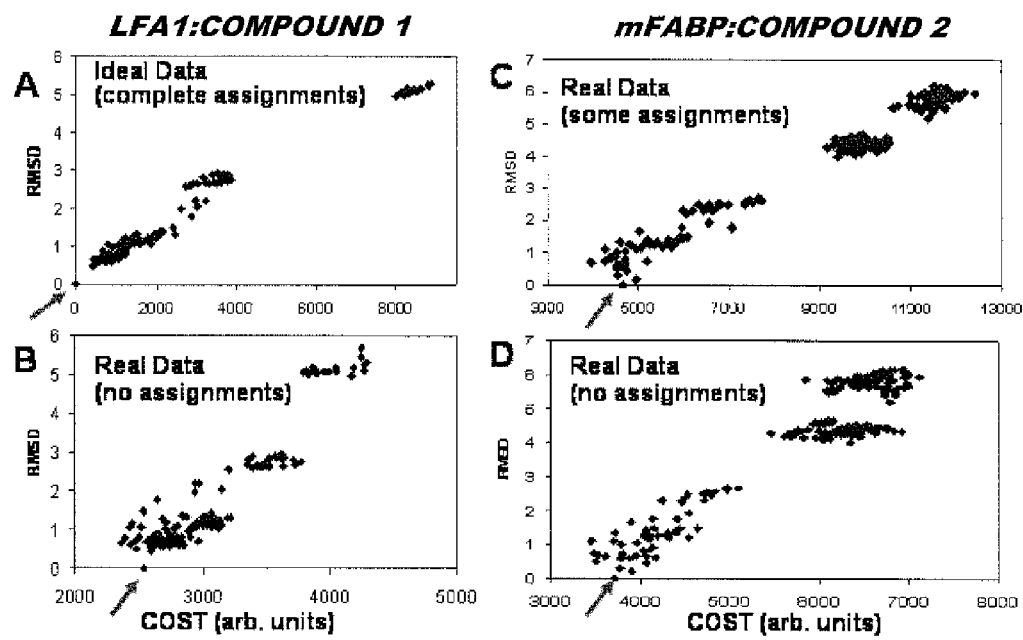
FIGS. 6A-6D depict selected results for the LFA1/Compound 1 and mFABP/Compound 2 test cases. Each panel shows the RMSD to the target binding mode (vertical axis) plotted against the COST of each binding mode (equation 6). Each mode is represented by a diamond. For both systems, a single member of the high resolution NMR ensemble (arrows, RMSD=0 Å) was chosen as the target binding mode.

Selected results from studies of both systems are shown in FIG. 6. For both systems, there is a clear correlation between the RMSD to the target binding mode and the COST, even when all of the predicted chemical shifts and standard deviations are derived from the BMRB.

With appropriate parameter values, the method is able to distinguish Compound 1/LFA1 and Compound 2/mFABP binding modes that are similar to the target experimental mode from those that are dissimilar from the target mode. The best scoring modes show low RMSD values to the target modes, and the target modes score well. For binding modes similar to the target mode, a significant number of NOE interactions were correctly assigned. These results hold even when the predicted shifts and their associated errors are derived from the averages and the standard deviations given in the BMRB. These studies indicate that the method yields a meaningful structural interpretation of protein-ligand NOE data without sequence specific protein NMR assignments Laboratory Example 2

The present inventors obtained a solution structure ensemble of the LFA1 I-domain complexed with Compound 3. The NMR spectrum of the protein-ligand complexed was assigned using a rapid assignment protocol that allowed the assignment of a subset of the protein-ligand NOE interactions. Backbone HN assignments were obtained by utilizing the determined assignments for the apo-protein, and recording a series of HSQC during a ligand titration. The ligand was in fast exchange. Initial backbone-sidechain scalar connectivities were established by CBCACONH and HBHACONH experiments. Protein side-chains known to be in the binding pocket were then assigned by interactive analysis of HCCH TOCSY spectra.

A total of 45 protein-ligand NOE restraints were obtained, of which 13 contain assignment ambiguities due to resonance overlaps. Key interactions include strong NOEs between the Compound 3 isopropyl group and the methyl groups of V130, L132 and V233, and a medium intensity NOE between the un-substituted Compound 3 aromatic ring and I259. Restrained simulated annealing calculations were performed using X-PLOR (Molecular Simulations, Inc. Burlington, Mass.). Out of 100 structures calculated, 29 were selected that had total energies <330.0 kcal/mole and NOE restraint energies <1.0 kcal/mole.

Figure 7:
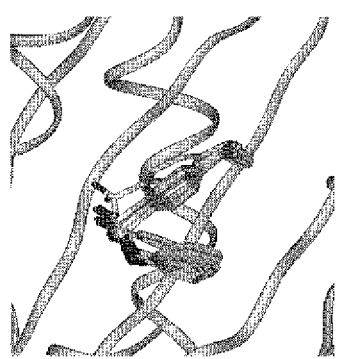
FIG. 7 depicts three clusters of NMR structures for the Compound 3/LFA1 complex. A portion of the protein backbone is shown as a ribbon, and the Compound 3 structures are shown as stick diagrams.
Figure 7:
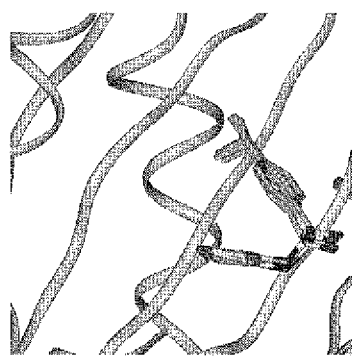
Figure 7:
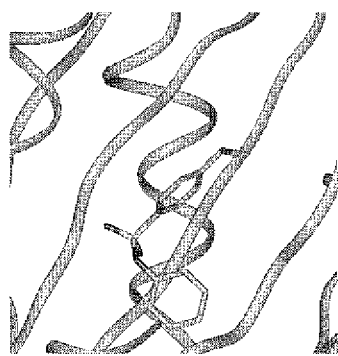

Distinct clusters of structures were obtained (FIG. 7). In order to identify the structures that are consistent with the complete set of intermolecular NOE peaks, the NOE matching algorithm was applied to the 29 NMR structures.

The results of the NOE matching algorithm indicate that clusters 1 and 3 (FIG. 7) are in better agreement with the experimental data than cluster 2.

What is claimed is:

1. A computer-implemented method of determining a preferred binding pose of a ligand in a complex comprising a target protein and a ligand using non-scalar magnetic couplings, comprising:
   (a) assigning the NMR resonance shifts of the ligand;
   (b) acquiring data from an observed NMR peak pattern comprising target protein resonances and ligand resonances using an NMR spectrometer, the peak pattern indicating non-scalar couplings between the nuclei of a sample comprising a target protein and a ligand, without requiring assignments for the NMR resonances of the target protein;
   (c) designating a set of three-dimensional, structural coordinates for one or more trial binding poses for at least a portion of the protein-ligand complex;
   (d) predicting an NMR peak pattern arising from non-scalar couplings between the target protein and the ligand in its designated trial binding pose,
   (e) finding the optimal match between the predicted peak pattern with the observed peak pattern using an equally partitioned bipartite weighted matching algorithm;
   (f) based on the match, assigning the trial binding pose a quantitative score representing the degree of similarity between the observed and predicted peak patterns;
   (g) repeating steps (c) through (f) a desired number of times to generate a quantitative score for each of one or more binding poses; and
   (h) evaluating the relative quantitative scores to identify one or more binding poses that are the most consistent with the observed peak pattern,
   wherein one or more of steps (a) through (h) are performed by a computer programmed to carry out each step.

2. The method of claim 1, wherein the ligand is bound to a target protein in the observed peak pattern.

3. The method of claim 1, wherein the ligand is exchanging between target-bound and unbound states in the observed peak pattern, and wherein a sufficient amount of the ligand is bound to the protein to permit observation of non-scalar couplings between said ligand and said target protein.

4. The method of claim 1, wherein the target protein resonances are acquired by employing a method selected from the group consisting of:
   (a) estimating target protein resonance shifts from available data;
   (b) predicting target protein resonance shifts in silico;
   (c) experimentally determining target protein resonances; and
   (d) a combination of two or more of (a), (b) and (c).

5. The method of claim 1, wherein the step of acquiring an observed NMR peak pattern further comprises grouping observed target protein resonances on the basis of magnetic similarity.

6. The method of claim 1, wherein the observed NMR peak pattern is derived from one of:
   (a) one or more 3D $^{13}$C-edited, $^{15}$N/$^{13}$C-filtered HSQC-NOESY spectra; and
   (b) one or more 2D $^{1}$H-$^{1}$H NOESY spectra.

7. The method of claim 1, wherein the observed NMR peak pattern comprises peaks clustered on the basis of one of:
   (a) the observed protein shifts; and
   (b) the observed protein shifts and additional information on the peak origins.

8. The method of claim 1, wherein the trial ligand binding pose is generated by performing an in silico operation to define an orientation and conformation of the ligand at a selected location relative to a three-dimensional structure of all or a portion of the target protein.

9. The method of claim 8, wherein the in silico operation is selected from the group consisting of:
   (a) modeling without experimentally-derived restraints;
   (b) modeling with experimentally-derived restraints included;
   (c) an in silico docking procedure; and
   (d) a combination of two or more of (a), (b) and (c).

10. The method of claim 9, wherein the in silico operation employs experimentally-derived data alone or in combination with one or more of a modeling procedure and an in silico docking procedure.

11. The method of claim 1, wherein the step of predicting an NMR peak pattern is performed in silico.

12. The method of claim 1, wherein the step of predicting an NMR peak pattern comprises the steps of:
  (a) obtaining target protein NMR resonance shifts;
  (b) obtaining and assigning target ligand NMR resonance shifts;
  (c) selecting a target protein nucleus and a ligand nucleus to form a protein-ligand pair;
  (d) predicting the peak intensity of a proposed magnetic interaction between each member of the pair;
  (e) predicting peak shifts for the proposed magnetic interaction;
  (f) placing each predicted peak in a pattern, the predicted peak being representative of the predicted peak intensity and predicted peak shift; and
  (g) repeating steps (c) through (f) for each of a selected number of protein-ligand pairs.

13. The method of claim 12, wherein the step of obtaining target ligand NMR resonance shifts comprises determining the $^1$H shifts by:
  (a) employing data obtained from two-dimensional (2D) double-$^{15}$N/$^{13}$C-filtered through-bond and through space correlated NMR spectra; and
  (b) employing data obtained from 2D $^1$H-$^1$H through-bond and through-space spectra recorded using $^2$H-labeled protein samples.

14. The method of claim 12, wherein the target protein nucleus is a group of magnetically-similar nuclei.

15. The method of claim 12, wherein the ligand nucleus is a group of magnetically-similar nuclei.

16. The method of claim 12, wherein the peak intensity is based on intermolecular distances between the groups of nuclei.

17. The method of claim 12, wherein the step of predicting peak shifts comprises estimating peak shifts by employing one or more of a database, an algorithm for chemical shift prediction, and experimental data.

18. The method of claim 1, wherein the step of matching the predicted peak pattern with the observed peak pattern using an equally partitioned bipartite weighted matching algorithm comprises:
  (a) arranging into an equally partitioned bipartite graph groups of protein nuclei observed to give rise to intermolecular non-scalar magnetic couplings and groups of protein nuclei predicted to give rise to intermolecular non-scalar magnetic couplings, wherein the protein groups observed to produce intermolecular non-scalar magnetic couplings are placed in a first subset of nodes, and the protein groups predicted to produce intermolecular non-scalar magnetic couplings placed in a second subset of nodes;
  (b) mapping the first subset of nodes to the second subset of nodes using a bipartite graph weighted matching algorithm that deterministically finds the optimal match in polynomial time; and
  (c) assigning the trial binding pose a quantitative score representing the degree of similarity between the observed and predicted peak patterns; the quantitative score for the optimal complete matching between the node subsets being based on an evaluation of deviations between observed and predicted peak patterns.

19. The method of claim 1, wherein the step of assigning the trial binding pose a quantitative score is combined with analysis of the structural similarities of the best scoring poses to evaluate the number of representative poses that are consistent with the experimental data.

20. The method of claim 1, wherein the method is employed in a high-throughput structure determination operation.

21. A method of determining a preferred binding pose of a ligand in a complex comprising a target protein and a ligand using non-scalar magnetic couplings, comprising:
  (a) assigning the NMR resonance shifts of the ligand;
  (b) acquiring data from an observed NMR peak pattern comprising target protein resonances and ligand resonances using an NMR spectrometer, the peak pattern indicating non-scalar couplings between the nuclei of a sample comprising a target protein and a ligand, without requiring assignments for the NMR resonances of the target protein;
  (c) designating a set of three-dimensional, structural coordinates for one or more trial binding poses for at least a portion of the protein-ligand complex;
  (d) predicting an NMR peak pattern arising from non-scalar couplings between the target protein and the ligand in its designated trial binding pose,
  (e) finding the optimal match between the predicted peak pattern with the observed peak pattern using an equally partitioned bipartite weighted matching algorithm;
  (f) based on the match, assigning the trial binding pose a quantitative score representing the degree of similarity between the observed and predicted peak patterns;
  (g) repeating steps (c) through (f) a desired number of times to generate a quantitative score for each of one or more binding poses; and
  (h) evaluating the relative quantitative scores to identify one or more binding poses that are the most consistent with the observed peak pattern.

22. The method of claim 21, wherein the ligand is bound to a target protein in the observed peak pattern.

23. The method of claim 21, wherein the ligand is exchanging between target-bound and unbound states in the observed peak pattern, and wherein a sufficient amount of the ligand is bound to the protein to permit observation of non-scalar couplings between said ligand and said target protein.

24. The method of claim 21, wherein the target protein resonances are acquired by employing a method selected from the group consisting of:
  (a) estimating target protein resonance shifts from available data;
  (b) predicting target protein resonance shifts in silico;
  (c) experimentally determining target protein resonances; and
  (d) a combination of two or more of (a), (b) and (c).

25. The method of claim 21, wherein the step of acquiring an observed NMR peak pattern further comprises grouping observed target protein resonances on the basis of magnetic similarity.

26. The method of claim 21, wherein the observed NMR peak pattern is derived from one of:
  (a) one or more 3D $^{13}$C-edited, $^{15}$N/$^{13}$C-filtered HSQC-NOESY spectra; and
  (b) one or more 2D $^1$H-$^1$H NOESY spectra.

27. The method of claim 21, wherein the observed NMR peak pattern comprises peaks clustered on the basis of one of:
  (a) the observed protein shifts; and
  (b) the observed protein shifts and additional information on the peak origins.

28. The method of claim 21, wherein the trial ligand binding pose is generated by performing an in silico operation to define an orientation and conformation of the ligand at a selected location relative to a three-dimensional structure of all or a portion of the target protein.

29. The method of claim 28, wherein the in silico operation is selected from the group consisting of:
  (a) modeling without experimentally-derived restraints;
  (b) modeling with experimentally-derived restraints included;
  (c) an in silico docking procedure; and
  (d) a combination of two or more of (a), (b) and (c).

30. The method of claim 29, wherein the in silico operation employs experimentally-derived data alone or in combination with one or more of a modeling procedure and an in silico docking procedure.

31. The method of claim 21, wherein the step of predicting an NMR peak pattern is performed in silico.

32. The method of claim 21, wherein the step of predicting an NMR peak pattern comprises the steps of:
  (a) obtaining target protein NMR resonance shifts;
  (b) obtaining and assigning target ligand NMR resonance shifts;
  (c) selecting a target protein nucleus and a ligand nucleus to form a protein-ligand pair;
  (d) predicting the peak intensity of a proposed magnetic interaction between each member of the pair;
  (e) predicting peak shifts for the proposed magnetic interaction;
  (f) placing each predicted peak in a pattern, the predicted peak being representative of the predicted peak intensity and predicted peak shift; and
  (g) repeating steps (c) through (f) for each of a selected number of protein-ligand pairs.

33. The method of claim 32, wherein the step of obtaining target ligand NMR resonance shifts comprises determining the $^1$H shifts by:
  (a) employing data obtained from two-dimensional (2D) double-$^{15}$N/$^{13}$C-filtered through-bond and through space correlated NMR spectra; and
  (b) employing data obtained from 2D $^1$H-$^1$H through-bond and through-space spectra recorded using $^2$H-labeled protein samples.

34. The method of claim 32, wherein the target protein nucleus is a group of magnetically-similar nuclei.

35. The method of claim 32, wherein the ligand nucleus is a group of magnetically-similar nuclei.

36. The method of claim 32, wherein the peak intensity is based on intermolecular distances between the groups of nuclei.

37. The method of claim 32, wherein the step of predicting peak shifts comprises estimating peak shifts by employing one or more of a database, an algorithm for chemical shift prediction, and experimental data.

38. The method of claim 21, wherein the step of matching the predicted peak pattern with the observed peak pattern using an equally partitioned bipartite weighted matching algorithm comprises:
  (a) arranging into an equally partitioned bipartite graph groups of protein nuclei observed to give rise to intermolecular non-scalar magnetic couplings and groups of protein nuclei predicted to give rise to intermolecular non-scalar magnetic couplings, wherein the protein groups observed to produce intermolecular non-scalar magnetic couplings are placed in a first subset of nodes, and the protein groups predicted to produce intermolecular non-scalar magnetic couplings placed in a second subset of nodes;
  (b) mapping the first subset of nodes to the second subset of nodes using a bipartite graph weighted matching algorithm that deterministically finds the optimal match in polynomial time; and
  (c) assigning the trial binding pose a quantitative score representing the degree of similarity between the observed and predicted peak patterns; the quantitative score for the optimal complete matching between the node subsets being based on an evaluation of deviations between observed and predicted peak patterns.

39. The method of claim 21, wherein the step of assigning the trial binding pose a quantitative score is combined with analysis of the structural similarities of the best scoring poses to evaluate the number of representative poses that are consistent with the experimental data.

40. The method of claim 21, wherein the method is employed in a high-throughput structure determination operation.

* * * * *